(12) United States Patent
Chen et al.

(10) Patent No.: US 8,461,362 B2
(45) Date of Patent: Jun. 11, 2013

(54) PROTEIN PHOSPHATASE 2A-ACTIVATING AGENTS

(75) Inventors: Ching-Shih Chen, Upper Arlington, OH (US); Dasheng Wang, Dublin, OH (US); Samuel K. Kulp, Hilliard, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 415 days.

(21) Appl. No.: 12/758,858

(22) Filed: Apr. 13, 2010

(65) Prior Publication Data

US 2010/0267673 A1 Oct. 21, 2010

Related U.S. Application Data

(60) Provisional application No. 61/168,759, filed on Apr. 13, 2009.

(51) Int. Cl.
- C07D 311/72 (2006.01)
- A61K 31/353 (2006.01)
- A61K 31/355 (2006.01)

(52) U.S. Cl.
USPC .......................................... 549/407; 514/456

(58) Field of Classification Search
USPC .......................................... 549/407; 514/456
See application file for complete search history.

(56) References Cited

U.S. PATENT DOCUMENTS

| | | | |
|---|---|---|---|
| 2,680,749 | A | 6/1954 | Cawley et al. |
| 4,262,017 | A | 4/1981 | Kulpers et al. |
| 4,751,224 | A | 6/1988 | Agarwal et al. |
| 6,004,565 | A | 12/1999 | Chiba et al. |
| 6,121,329 | A | 9/2000 | Fujii et al. |
| 6,417,223 | B1 | 7/2002 | Sanders et al. |
| 6,476,004 | B1 | 11/2002 | Sakai et al. |
| 6,645,998 | B2 | 11/2003 | Sanders et al. |
| 6,703,384 | B2 | 3/2004 | Sanders et al. |
| 6,770,672 | B1 | 8/2004 | Sanders et al. |
| 6,858,227 | B1 | 2/2005 | Lal et al. |
| 2004/0235938 | A1 | 11/2004 | Sanders et al. |
| 2004/0248971 | A1 | 12/2004 | Yeh et al. |
| 2005/0065149 | A1 | 3/2005 | Wang et al. |
| 2005/0090520 | A1 | 4/2005 | Lindquist |
| 2005/0215531 | A1 | 9/2005 | Baumruker et al. |
| 2008/0009545 | A1 | 1/2008 | Chen et al. |
| 2008/0161349 | A1 | 7/2008 | Sanders et al. |
| 2009/0137530 | A1 | 5/2009 | Kiuchi et al. |
| 2010/0022655 | A1 | 1/2010 | Byrd et al. |
| 2010/0179216 | A1 | 7/2010 | Kiuchi et al. |
| 2010/0267820 | A1 | 10/2010 | Chen et al. |
| 2010/0273871 | A1 | 10/2010 | Chen et al. |

FOREIGN PATENT DOCUMENTS

| | | |
|---|---|---|
| JP | 59-222415 | 12/1984 |
| WO | 01/58889 | 8/2001 |
| WO | 03/039461 | 5/2003 |
| WO | 2007/098139 | 8/2007 |
| WO | 2007/143081 | 12/2007 |
| WO | 2008/021532 | 2/2008 |
| WO | 2010/042998 | 4/2010 |
| WO | 2010/120711 | 10/2010 |
| WO | 2010/121111 | 10/2010 |

OTHER PUBLICATIONS

International Search Report and Written Opinion from PCT/US11/62304 dated Jun. 28, 2012.
Suzuki et al., "A novel immunosuppressant FTY720, with a unique mechanism of action, induces long-term graft acceptance in rat and dog allotransplantation", Transplantation, 61: pp. 200-205 (1996).
Suzuki et al., "Long-term graft acceptance in allografted rats and dogs by treatment with a novel immunosuppressant, FTY720. Transplantation Proceedings, 28: 1375-1376, 1996."
Suzuki et al., "Induction of lymphocyte apoptosis and prolongation of allograft survival by FTY720. Transplantation Proceedings, 28: 2049-2050, 1996."
Suzuki et al., "Immunosuppressive effect of a new drug, FTY720, on lymphocyte responses in vitro and cardiac allograft survival in rats. Transplant Immunology, 4: 252-255, 1996."
Takabe et al., "'Inside-out' signaling of sphingosine-1-phosphate: therapeutic targets", Pharmacol Rev 60, pp. 181-195 (2008).
Tchou et al., "GSTP1 CpG island DNA hypermethylation in hepatocellular carcinomas", Int J Onjcol, 16, pp. 663-676 (2000).
Tedesco-Silva et al., "FTY720, a novel immunomodulator: efficacy and safety results from the first phase 2A study in de novo renal transplantation. Transplantation, 77: 1826-1833, 2004."
Tedesco-Silva et al., FTY720, a novel immunomodulator: efficacy and safety results from the first phase 2A study in de novo renal transplantation. Transplantation, 79: 1553-1560, 2005.
Thomas, et al., "Drug-induced apoptosis in B-cell chronic lymphocytic leukemia: relationship between p53 gene mutation and bcl-2/bax proteins in drug resistance", Oncogene 12: pp. 1055-1062 (1996).
Thomas, et al., "Opportunities for Targeted Therapies in Hepatocellular carcinoma", J. Clin Oncol. 23, pp. 8093-8108 (2005).

(Continued)

Primary Examiner — Bernard Dentz
(74) Attorney, Agent, or Firm — Tarolli, Sundheim, Covell & Tummino LLP

(57) ABSTRACT

Tocopheryl succinate derivatives according to formula I:

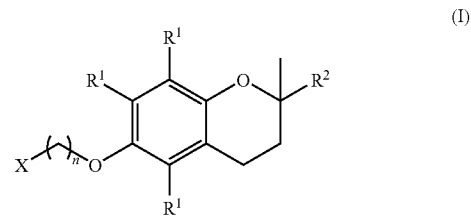

are described. These compounds increase the activity of protein phosphatase 2A, can be included in pharmaceutical compositions, and can be used for the treatment of androgen receptor-dependent cancers such as prostate cancer.

10 Claims, 4 Drawing Sheets

OTHER PUBLICATIONS

Tseng et al., "Overcoming trastuzumab resistance in HER2-overexpressing breast cancer cells by using a novel celecoxib-derived phosphoinositide-dependent kinase-1 inhibitor", Mol Pharmacol 70, pp. 1534-1541 (2006).

Varga et al., "Tumor grade-depdneent alterations in the protein kinase C isoform pattern in urinary bladder carcinomas", Eur Urol 46, pp. 462-465 (2004).

Weber et al., "Induction of cancer cell apoptosis by alpha-tocopheryl succinate: molecular pathways and structural requirements", FASEB. J., 15 (2) Feb. 2001.

Yasui et al., "FTY720 induces apoptosis in multiple myeloma cells and overcomes drug resistance", Cancer Research, 65: 7478-7484 (2005).

Yusof et al., "Immunohistochemical expression of π class glutathione S-transferase and α-Fetoprotein in hepatocellular carcinoma and chronic liver disease", Anal Quant Cytol Histol, 25, pp. 332-338 (2003).

Zhou et al., "FTY720, a fungus metabolite, inhibits invasion ability of androgen-independent prostate cancer cells through inactivation of RhoA-GTPase", Cancer Letters, 233: 36-47 (2006).

International Search Report and Written Opinion from PCT/US07/04337 dated Sep. 19, 2008.

International Search Report and Written Opinion from PCT/US10/30799 dated May 18, 1010.

Interview Summary from U.S. Appl. No. 11/708,792 dated Apr. 9, 2009.

Office action from U.S. Appl. No. 11/708,792 dated Jul. 6, 2009.

Response to Office action from U.S. Appl. No. 11/708,792 dated Aug. 12, 2009.

Office action from U.S. Appl. No. 11/708,792 dated Nov. 27, 2009.

Communication from European Application No. 07751119.4 dated Mar. 13, 2009.

Arya P., et al., "Design and Synthesis of Analogs of Vitamin E: Antiproliferative Activity Against Human Breast Andenocarcinoma Cells", Bioorganic & Medicinal Chemistry Letters, vol. 8, 1998, pp. 2433-2438.

Bang et al., "Activiation of PKC but not of ERK is required for vitamin E-succinate-induced apoptosis of HL-60 cells", Biochem Biophys Res. Commun, 288, pp. 789-797 (2001).

Barnett et al., "Vitamin E succinate inhibits colon cancer liver metastases", J Surg Res 106, pp. 292-298 (2002).

Birringer et al., "Vitamin E analogues as inducers of apoptosis: structure-function relation", Br J Cancer 88, pp. 1948-1955 (2003).

Chen et al., "Molecular determinants of resistance to antiandrogen therapy," Nat. Med 10, pp. 33-39 (2004).

Wang et al., "A peptide conjugate of vitamin E succinate target breast cancer cells with high ErbB2 expression", Cancer Res 67, pp. 3337-3344 (2007).

Wang et al., "Vitamin E analogues as anticancer agents: lessons from studies with alpha-tocopheryl succinate", Mol. Nutr. Food Res., 50, pp. 675-685 (2006).

Chuang et al., "Phosphorylation by c-Jun NH2-terminal kinase 1 regulates the stability of transcription factor Sp1 during mitosis", Mol Biol Cell 19, pp. 1139-1151 (2008).

Crispen et al., "Vitamin E succinate inhibits NF-kappaB and prevents the development of a metastatic phenotype in prostate cancer cells: implications for chemoprevention", Prostate, 67, pp. 582-590 (2007).

Dalen et al., "Alpha-tocopheryl succinate sensitises a T lymphoma cell line to TRAIL-induced apoptosis by suppressing NF-kappB activation", Br. J Cancer 88, pp. 153-158 (2003).

Degterev et al., "Identification of small-molecule inhibitors of interaction between the BH3 domain and Bcl-x", Nat. Cell Biol, 3, pp. 173-182 (2001).

Dong et al., "Vitamin E analogues inhibit angiogenesis by selective induction of apoptosis in proliferating endothelial cells: the role of oxidative stress", Cancer Res 67, pp. 11906-11913 (2007).

Gu et al., "Vitamin E succinate induces ceramide-mediated apoptosis in head and neck squamous cell carcinoma in vitro and in vivo", Clin Cancer Res, 14, pp. 1840-1848 (2008).

Hahn et al., "Dietary administration of the proapoptotic vitamin E analogue alpha-tocopheryloxyacetic acid inhibits metastatic murine breast cancer", Cancer Res 66, pp. 9374-9378 (2006).

Huang et al., "a-Tocopheryl succinate and derivatives mediate the transcriptional repression of androgen receptor in prostate cancer cells by targeting the PP2A-JNK-Sp1 Signaling axis", Carcinogenesis, vol. 30, No. 7, pp. 1125-1131, 2009.

Janssens et al., "Protein phosphatase 2A: a highly regulated family of serine/threonine phosphatases implicated in cell growth and signalling", Biochem J, 353, pp. 417-439 (2001).

Juntilla et al., "CIP2A inhibits PP2A in human malignancies", Cell, 130, pp. 51-62 (2007).

Kogure et al., "Potentiation of anti-cancer effect by intravenous administration of vesiculated tocophyeryl hemisuccinate on mouse melanoma in vivo", Cancer Lett, 192, pp. 19-24 (2003).

Lawson et al., "Novel vitamin E analogue decreases syngeneic mouse mammary tumor burden and reduces lung metastasis", Mol Cancer Ther, 2, pp. 437-444 (2003).

Lei et al., "The Bax subfamily of Bcl2-related proteins is essential for apoptotic signal transduction by c-Jun NH(2)-terminal kinase", Mol Cell Biol, 22, pp. 4929-4942 (2002).

Lugovskoy et al., "A Novel approach for characterizing protein ligand complexes: Molecular basis for specificity of small-molecule Bcl-2 inhibitors", J Am Chem Soc, 124, pp. 1234-1240 (2002).

Malafa et al., "Vitamin E succinate promotes breast cancer tumor dormancy", J Surg Res, 93, pp. 163-170 (2000).

Malafa et al., "Inhibition of angiogenesis and promotion of melanoma dormancy by vitamin E succinate", Ann Surg Oncol 9, pp. 1023-1032 (2002).

Mumby, M., "PP2A: unveiling a reluctant tumor suppressor", Cell, 130, pp. 21-24 (2007).

Neuzil et al., "Induction of cancer cell apoptosis by alpha-tocopheryl succinate: molecular pathways and structural requirements", FASEB J, 15, pp. 403-415 (2001.

Neuzil et al., "Selective cancer cell killing by tocopheryl succinate", Br. J. Cancer, 84, pp. 87-89 (2001).

Neuzil et al., "a-Tocopheryl succinate epitomizes a compound with a shift in biological activity due to pro-vitamin-to-vitamin conversion", Biochem Biophys Res Commun, 293, pp. 1309-1313 (2002).

Neuzil et al., "Vitamin E analogs, a novel group of "mitocans," as anticancer agents: the importance of being redox-silent", Mol Pharmacol, 71: pp. 1185-1199 (2007).

Ni et al., "Vitamin E succinate inhibits human prostate cancer cell growth via modulating cell cycle regulatory machinery", Biochem Biophys Res Commun, 300, pp. 357-363 (2003).

Prasad et al., "Effects of tocopherol (Vitamin E) acid succinate on morphological alterations and growth inhibition in melanoma cells in culture", Cancer Res 42, pp. 550-555 (1982).

Prasad et al., "a-Tocopheryl succinate, the most effective form of vitamin E for adjuvant cancer treatment: A review", J Am Coll Nutr 22, pp. 108-117 (2003).

Qian et al., "c-Jun involvement in vitamin E succinate induced apoptosis of reticuloendotheliosis virus transformed avian lymphoid cells", Oncogene 15, pp. 223-230 (1997).

Shanker et al., "Vitamin E succinate in combination with mda-7 results in enhanced human ovarian tumor cell killing through modulation of extrinsic and intrinsic apoptotic pathways", Cancer Lett, 254, pp. 217-226 (2007).

Shiau et al., "a-tocopheryl succinate induces apoptosis in prostate cancer cells in part through inhibition of Bcl-xL/ Bcl-2 function", J Biol Chem, 281, pp. 11819-11825 (2006).

Wang et al., Carcinogenesis, 27, pp. 2124-2132 (2006).

Wang et al., "a-Tocopheryl succinate as a scaffold to develop potent inhibitors of breast cancer cell adhesion", J Med Chem 52, pp. 5642-5648 (2009).

Weber et al., "Vitamin E succinate is a potent novel antineoplastic agent with high selectivity and cooperativity with tumor necrosis factor-related apoptosis-inducing ligang (Apo2 ligand) in vivo", Clin Cancer Res 8, pp. 863-869 (2002).

Weber et al., "Mitochondria play a central role in apoptosis induced by alpha-tocopheryl succinate, an agent with antineoplastic activity: comparison with receptor-mediated pro-apoptotic signaling", Biochemistry, 42, pp. 4277-4291 (2003).

Wu et al., "Cellular and molecular effects of alpha-tocopheryloxybutyrate: Lessions for the design of vitamin E analog for cancer prevention", Anticander Research, Helenic Anticancer Institute, Athens, vol. 24, No. 6, Nov. 1, 2004 pp. 3795-3802.

Yin et al., "The therapeutic and preventive effect of RRR-alpha-vitamin E succinate on prostate cancer via induction of insulin-like growth factor binding protein-3", Clin Cancer Res, 13, pp. 2271-2280 (2007).

You et al., "RRR-alpha-tocopheryl succinate induces MDA-MB-435 and MCF-7 human breast cancer cells to undergo differentiation", Cell Growth Differ, 12, pp. 471-480 (2001).

You et al., "Role of extracellular signal-regulated kinase pathway in RRR-alpha-tocopheryl succinate-induced differentation of human MDA-MB-435 breat cancer cells", Mol Carcinog, 33, pp. 228-236 (2002).

Yu et al., "Activation of extracellular signal-regulated kinase and c-Jun-NH(2)-terminal kinase but not p38 mitogen-activiated protein kinases is required for RRR-alpha-tocopheryl succinate-induced apoptosis of human breast cancer cells", Cancer Res 61, pp. 6569-6576 (2001).

Zhang et al., "Vitamin E succinate inhibits the function of androgen receptor and the expression of prostate-specific antigen in prostate cancer cells", Proc Natl Acad Sci USA, 99, pp. 7408-7413 (2002).

Zhao et al., "alpha-tocopheryl succinate-induced apoptosis in human gastric cancer cells is modulated by ERK1/2 and c-Jun N-terminal kinase in a biphasic manner", Cancer Lett, 247, pp. 345-352 (2007).

Zolnierowicz, S., "Type 2A protein phosphatase, the complex regulator of numerous signaling pathways", Biochem Pharmacol, 60: pp. 1225-1235 (2000).

European Search Report from Application 10765245.5 dated Jul. 11, 2012.

Genini et al., "Nucleotide requirements for the in vitro activation of the apoptosis protein-activating factor-1-mediated caspase pathway. The Journal of Biological Chemistry, 275: 29-34, 2000".

Haynes et al., "Occurrence of pharmaceutically acceptable annions and cations in the Cambridge structural database", J Pharm Sci, 94, pp. 2111-2120 (2005).

Ho et al., "Effects of a novel immunomodulating agent, FTY720, on tumor growth and angiogenesis in hepatocellular carcinoma", Molecular Cancer Therapeutics, 4: 1430-1438 (2005).

Hoshino et al., "FTY720, a novel immunosuppressant possessing unique mechanims. II. Long-term graft survival induction in rat heterotopic cardiace allografts and synergistic effect in combination with cyclosporine A", Transplantation Proceedings, 28: pp. 1060-1061 (1996).

Hung et al., FTY720 induces apoptosis in hepatocellular carcinoma cells through activation of protein kinase Cδ signaling, Cancer Res 68, pp. 1204-1212 (2008).

Jackson et al., "The enigmatic protein kinase Cδ: complex roles in cell proliferation and survival", FASEB J, 18, pp. 627-636 (2004).

Johnson et al., "A novel celecoxib derivative, OSU03012, induces cytotoxicity in primary CLL cells and transformed B-cell lymphoma cell line via a caspase- and Bcl-2-independent mechanism", Blood, v.105, p. 2504-2509 (2005).

Kahan et al., "Pharmacodynamics, pharmacokinetics, and safety of multiple doses of FTY720 in stable renal transplant patients: a multicenter, randomized, placebo-controlled, phase I study. Transplantation, 76: 1079-1084, 2003".

Kawaguchi et al., "FTY720, a novel immunosuppressant possessing unique mechanisms. III. Synergistic prolongation of canine renal allograft survival in combination with cyclosporine A", Transplantation Proceedings 28: pp. 1062-1063 (1996).

Kitada et al. "Expression of apoptosis-regulating proteins in chronic lymphocytic leukemia: correlations with In vitro and In vivo chemoresponses", Blood, 91: 3379-3389 (1998).

Kiuchi et al., "Synthesis and immunosuppressive activity of 2-substituted 2-aminopropane-1, d-diols and 2-aminoethanols", J Med Chem 43, pp. 2946-2961 (2000).

Koopman et al., Annexin V for flow cytometric detection of phosphatidylserine expression on B cells undergoing apoptosis. Blood, 84: 1415-1420, 1994.

Lee et al., "FTY720 induces apoptosis of human hepatoma cell lines through Pl3-K-mediated Akt dephosphorylation", Carcinogenesis, 25: 2397-2405 (2004).

Lee et al., "Significance of the Rac signaling pathway in HCC cell motility: implications for a new therapeutic target", Carcinogenesis, 26: 681-687 (2005).

Lee et al., "FTY720: a promising agent for treatment of metastatic hepatocellular carcinoma. Clinical Cancer Research : an Official Journal of the American Association for Cancer Research", 11: 8458-8466 (2005).

Li et al., "The myeloid leukemia-associated protein SET is a potent inhibitor of protein phosphatase 2A", J. Biol. Chem. 271, pp. 11059-11062 (1996).

Li et al., "Induction of lymphocyte apoptosis by a novel immunosuppressant FTY720: relation with Fas, Bcl-2 and Bax expression", Transplantation Proceedings, 29: 1267-1268 (1997).

Li Dengju et al., "Role of extracellular regulated protein kinases in FTY720-induced apoptosis of leukemia cell lines HL-60 and U937", Journal of Huazhong University of Science and Technology [Med Sci], 24, p. 45-47 (2004).

Liu, "Small molecule antagonists of LFA-1/ICAM-1 interactions as potential therapeutic agents", Expert Opinion Ther. Patents, 11 (9): pp. 1383-1393 (2001).

Llovet et al., "Sorafenib in advanced hepatocellular carcinoma", N Engl J Med, 359, pp. 378-390 (2008).

Martin, R., "Closing in on an oral treatment" Multiple Sclerosis, Nature 464, pp. 360-362 (2010).

Masubuchi et al., "FTY720, a novel immunosuppressant, possessing unique mechanisms. IV. Prevention of graft versus host reactions in rats. Transplantation Proceedings, 28: 1064-1065, 1996".

Matsuoka et al., "Reduction of phosphorylated Akt/PKB by immunosuppressant FTY720" Cell Biology International, 24, p. 976-977 (2000).

Matsuoka et al, "A novel immunosuppressive agent FTY720 induced Akt dephosphorylation in leukemia cells", British Journal of Pharmacology, 138: 1303-1312 (2003).

McConkey, et al., "Apoptosis sensitivity in chronic lymphocytic leukemia is detrmined by endogenous endonuclease content and relative expression of BCL-2 and BAX", J. Immunol. 156: pp. 2624-2630 (1996).

Moon et al., "PDE4 inhibitors activate a mitochondrial apoptotic pathway in chronic lymphocytic leukemia cells that is regulated by protein phosphatase 2A", Blood 101, pp. 4122-4130 (2003).

Morley et al., "Proteasome inhibitors and immunosuppressive drugs promote the cleavage of elF4GI and elF4GII by caspase-8-independent mechanisms in Jurkat T cell lines" FEBS Letters, 503: 206-212 (2001).

Mullershausen et al., "Persistent signaling induced by FTY720-phosphate is mediated by internalized S1P1 receptors", Nat Chem Biol 5, pp. 428-434 (2009).

Nagahara et al., "Evidence that FTY720 induces T cell apoptosis in vivo", Immunopharmacology, 48: 75-85 (2000).

Nagahara et al., "Immunosuppressant FTY720 induces apoptosis by direct induction of permeability transition and release of cytochrome c from mitochondria", Journal of Immunology, 165, p. 3250-3259 (2000).

Nagahara et al., "Coordinate involvement of cell cycle arrest and apoptosis strengthen the effect of FTY720", Japanese Journal of Cancer Research : 92: 680-687 (2001).

Nagahara et al., "T cell selective apoptosis by a novel immunosuppressant, FTY720, is closely regulated with Bcl-2", British Journal of Pharmacology, 137: 953-962 (2002).

Omar et al., "Targeting of the Akt-nuclear factor-κB signaling network by [1-(4-chloro-3-nitrobenzenesulfonyl)-1H-indol-3-yl]-methanol (OSU-A9), a novel indole-3-carbinol derivative, in a mouse model in hepatocellualr carcinoma", Mol Phamacol 76, pp. 957-968 (2009).

Pabst et al., "Enhanced FTY720-mediated lymphocyte homing requires G alpha i signaling and depends on beta 2 and beta 7 integrin", J. Immunol, 176: 1474-1480 (2006).

Prieschl, "The balance between sphingosine and sphingosine-1-phosphate is decisive for mast cell activation after Fcε receptor I triggering", J Exp Med 190, pp. 1-8 (1999).

Quesniaux et al, "The novel immunosuppressant FTY720 induces peripheral lymphodepletion of both T- and B-cells in cynomolgus monkeys when given alone, with Cyclosporine Neoral (R) or with RAD", Transplant Immunology, 8: 177-187 (2000).

Reno et al., "Analysis of protein kinase C delta (PKCδ) expression in endometrial tumors", Hum Pathol, 39, pp. 21-29 (2008).

Reyland, "Protein kinase Cδ and apoptosis", Biochem Soc Trans 35, pp. 1001-1004 (2007).

Salesse et al., "BCR/ABL-mediated increased expression of multiple known and novel genes that may contribute to the pathogenesis of chronic myelogenous leukemia", Molecular Cancer Therapeutics, v. 2, p. 173-182 (2003).

Schonthal, A. H., "Role of serine/threonine protein phosphatase 2A in cancer", Cancer Lett. 170, pp. 1-13 (2001).

Seitz et al., "Effects of sphingosine 1-phosphate (S1P) and expression of S1P receptors in chronic lymphocyte leukemia (B-CLL): potential role in cell trafficking and survival", Experimental Hemaology, 33, p. 99 (2005).

Skerjanec et al., "FTY720, a novel immunomodulator in de novo kidney transplant patients: pharmacokinetics and exposure-response relationship. Journal of Clinical Pharmacology, 45: 1268-1278, 2005".

Stoetzer et al., "Drug-induced apoptosis in chronic lymphocytic leukemia. Leukemia : Official Journal of the Leukemia Society of America, Leukemia Research Fund, U.K, 13: 1873-1880, 1999".

Suleiman et al., "FTY720 prevents renal T-cell infiltration after ischemia/reperfusion injury. Transplantation Proceedings, 37: 373-374, 2005".

Suzuki et al., "A new immunosuppressant, FTY720, induces bcl-2-associated apoptotic cell death in human lymphocytes", Immunology, 89: 518-523 (1996).

International Search Report for PCT/US2006/010882, mailed Feb. 9, 2007.

International Search Report and Written Opinion from PCT/US07/12921 dated Dec. 12, 2007.

International Search Report and Written Opinion from PCT/US10/31363 dated Jul. 13, 2010.

Office action from U.S. Appl. No. 12/302,953 dated Oct. 18, 2011.

Response from U.S. Appl. No. 12/302,953 dated Jan. 17, 2012.

Notice of Allowance from U.S. Appl. No. 12/302,953 dated Apr. 23, 2012.

Office action from U.S. Appl. No. 12/761,504 dated Apr. 11, 2012.

Office action from Australian Application No. 2007217810 dated Aug. 16, 2011.

Response from European Application No. 07751119.4 dated Feb. 17, 2010.

Extended European Search Report for European Application No. 07809273.1, dated Aug. 14, 2009.

Response to European Communication from 07809273.1 dated Sep. 22, 2010.

Ayllon et al., "Protein phosphatase 1 alpha is a Ras-activated Bad phosphatase that regulated interleukin-2 deprivation-induced apoptosis", The EMBO Journal, 19, pp. 2237-2246 (2000).

Azuma et al., "Marked prevention of tumor growth and metastasis by a novel immunosuppressive agent, FTY720, in mouse breast cancer models", Cancer Research, 62: 1410-1419 (2002).

Azuma et al. "Selective cancer cell apoptosis induced by FTY720; evidence for a Bcl-dependent pathway and impairment in ERK activity", Anticancer Research, 23: 3183-3193 (2003).

Baumhoer et al., "Glypican 3 expression in human nonneoplastic, preneoplastic, and neoplastic tissues", Am J Clin Pathol, 129, pp. 899-906 (2008).

Bellosillo et al., "Involvement of CED-3/ICE proteases in the apoptosis of B-chronic lymphocytic leukemia cells", Blood, 89: 3378-3384 (1997).

Boehler et al., "FTY720 alters the composition of T-lymphocyte subpopulations in the peripheral blood compartment of renal transplant patients", Transplantation Proceedings, 34: 2242-2243 (2002).

Bohler et al., "Pharmacodynamics of FTY720, the first member of a new class of immune-modulating therapeutics in transplantation medicine", International Journal of Clinical Pharmacology and Therapeutics, 41: 482-487 (2003).

Bohler et al., "FTY720 mediates apoptosis-independent lymphopenia in human renal allograft recipients: different effects on CD62L+ and CCR5+ T lymphocytes", Transplantation, 77: 1424-1432 (2004).

Braun, W.E, "Renal transplantation: basic concepts and evolution of therapy. J Clin Apher, 18: 141-152, 2003."

Brinkmann, V., "FTY720 alters lymphocyte homing and protects allografts without inducing general immunosuppression", Transplantation Proceedings, 33: 530-531 (2001).

Brinkmann et al., "The immune modulator FTY720 targets sphingosine 1-phosphate receptors", The Journal of Biological Chemistry, 277: 21453-21457 (2002).

Brinkmann, et al., "FTY720: targeting G-protein-coupled receptors for sphingosine 1-phosphate in transplantation and autoimmunity", Current Opinion in Immunology, 14: 569-575 (2002).

Brinkmann et al., "FTY720: sphingosine 1-phosphate receptor-1 in the control of lymphocyte egress and endothelial barrier function", American Journal of Transplantation; 4: 1019-1025 (2004).

Brinkmann, V. "FTY720: mechanism of action and potential benefit in organ transplantation", Yonsei Medical Journal, 45: 991-997 (2004).

Budde et al., First human trial of FTY720, a novel immunomodulator, in stable renal transplant patients. Journal of the American Society of Nephrology : JASN, 13: 1073-1083, 2002.

Budde et al., "Pharmacodynamics of single doses of the novel immunosuppressant FTY720 in stable renal transplant patients", American Journal of Transplantation; 3: 846-854 (2003).

Calabresi, et al., "Section IX Chemotherapy of Neoplastic Diseases—Introduction", Goodman & Gilman's The Pharmacological Basis of Theapeutics 10th ed, Hardman, et al., Eds, McGraw-Hill, NY, pp. 1381, 1383-1385 and 1388, (2001).

Carbrera et al., "Review article: the management of hepatocellular carcinoma", Aliment. Pharmacol. Ther. 31, pp. 461-476 (2010).

Cattan, et al., "The C.B.17 scid mouse strain as a model for human disseminated leukaemia and myeloma in vivo. Leukemia Research, 18: 513-522, 1994".

Cheson et al., "National Cancer Institute-sponsored Working Group guidelines for chronic lymphocytic leukemia: revised guidelines for diagnosis and treatment. Blood, 87: 4990-4997, 1996".

Cheson et al., "Myelodysplastic syndromes standardized response criteria: further definition. Blood, 98: 1985, 2001".

Chiang et al., "Protein phosphatase 2A acivates the proapoptotic function of BAD in interleukin-3-dependent lymphoid cells by a mechanism requiring 14-3-3 dissociation", Blood, 1289-1297 (2001).

Chiba et al., "FTY720, a novel immunosuppressant possessing unique mechanisms. I. Prolongation of skin allograft survival and synergistic effect in combination with cyclosporine in rats", Transplantation Proceedings, 28, pp. 1056-1059 (1996).

Chua et al., "FTY720, a fungus metabolite, inhibits in vivo growth of androgen-independent prostate cancer", International Journal of Cancer, 117: 1039-1048 (2005).

Chueh et al., "Induction of tolerance toward rat cardiac allografts by treatment with allochimeric class I MHC antigen and FTY720. Transplantation, 64: 1407-1414, 1997".

Cohen et al., "Oral fingolimod or intramuscular interferon for relapsing multiple sclerosis", N Engl J Med 362, pp. 402-415 (2010).

D'Costa et al., "The proapoptosis tumor suppressor protein kinase C-δ is lost in human squamous cell carcinomas", Oncogene 25, pp. 378-386 (2006).

Dragun et al., "FTY720: early clinical experience. Transplantation Proceedings, 36: 544S-548S, 2004".

Dragun et al., "FTY720-induced lymphocyte homing modulates post-transplant preveration/reperfusion injury", Kidney Int 65, pp. 1076-1083 (2004).

Enosawa et al., "Induction of selective cell death targeting on mature T-Iymphocytes in rats by a novel immunosuppressant, FTY720". Immunopharmacology, 34: 171-179 (1996).

Feschenko et al., "A novel cAMP-stimulated pathway in protein phosphatase 2A activation", J. Pharmacol. Exp. Ther. 302, pp. 111-118 (2002).

Ferguson, R., "FTY720 immunomodulation: optimism for improved transplant regimens. Transplantation Proceedings, 36: 549S-553S, 2004".

Fujino, et al., "Activation of caspases and mitochondria in FTY720-mediated apoptosis in human T cell line Jurkat", International Immunopharmacology, 1: 2011-2021 (2001).

Fujino et al., "Distinct pathways of apoptosis triggered by FTY720, etoposide, and anti-Fas antibody in human T-lymphoma cell line (Jurkat cells)", Journal of Pharmacology and Experimental Therapeutics, 300, p. 939-945 (2002).

PROTEIN PHOSPHATASE 2A-ACTIVATING AGENTS

CONTINUING APPLICATION DATA

This application claims the benefit of U.S. Provisional Patent Application No. 61/168,759, filed Apr. 13, 2009, which is incorporated by reference herein.

GOVERNMENT FUNDING

The present invention was made with government support under Grant No. CA12250, awarded by the National Cancer Institute (NCI) and Grant No. PC074151, awarded by the Department of Defense Prostate Cancer Research Program. The Government may have certain rights in this invention.

BACKGROUND

The translational potential of α-tocopheryl succinate (a.k.a., vitamin E succinate; VES) in cancer therapy has been the focus of many recent investigations in light of its efficacy in suppressing tumor cell proliferation without incurring toxicity to normal cells. See for example Wang et al., Mol. Nutr. Food Res., 50, 675-85 (2006). Substantial evidence indicates that VES exhibits a unique ability to target multiple signaling pathways associated with carcinogenesis, tumor progression, and metastasis, including those mediated by NF-κB, PKCα, sphingolipids, Bcl-2/Bcl-xL, androgen receptor (AR), vascular endothelial growth factor (VEGF), and insulin-like growth factor binding protein-3. Although some of these signaling targets might be cancer type-specific, this broad spectrum of action in conjunction with low toxicity underlies the therapeutic value of developing VES into useful agents for cancer treatment or prevention.

One of the cancers affected by VES is prostate cancer. A significant challenge in the management of patients with prostate cancer is the treatment of hormone-refractory prostate cancer (HRPC), a hallmark of incurable and lethal prostate cancer progression. To date, chemotherapeutic regimens provide substantive benefits through palliation, but yield no definitive enhancement in survival. A clear need exists for novel strategies that will improve the treatment of prostate cancer and ultimately increase the survival of prostate cancer patients. Accordingly, significant efforts have been expended to identify small-molecule agents targeting dysregulated pathways associated with HRPC.

The Ras signaling system provides a potential target for small molecule agents being developed for use against prostate cancer. The proto-oncogenic Ras functions as a molecular switch for signal transduction pathways controlling cell growth and differentiation, including those mediated by Akt, ERKs, RalA GTPase, and the transcription factor c-Myc. As these tumorigenic effectors of Ras regulate various aspects of oncogenesis in different cellular contexts, evidence indicates that Ras signaling represents a major driving force for prostate cancer progression to an androgen-independent state. Weber et al., J. Cell Biochem, 91, p. 13-25 (2004). Moreover, dominant negative inhibition of endogenous Ras activity has been shown to restore androgen sensitivity to hormone-refractory C4-2 prostate cancer cells. Bakin et al., Cancer Res., 63, p. 1975-80 (2003). Together, these finding indicate that Ras signaling represents a therapeutically relevant target for HRPC treatment.

Farnesyltransferase (FTase) inhibitors were originally developed as anti-Ras compounds and novel target-based drugs for cancer treatment. However, R115777, a potent FTase inhibitor, showed little anti-tumor activity in minimally pretreated patients with androgen-independent prostate cancer. This lack of clinical efficacy underlies uncertainty over whether Ras is a relevant target of FTase inhibitors in humans.

PP2A is a tumor suppressor that antagonizes Ras signaling. PP2A is a ubiquitously expressed protein serine/threonine phosphatase that accounts for a large fraction of phosphatase activity in human cells. Janssens et al., Biochem J., 353, p. 417-39 (2001). PP2A is composed of a dimeric core enzyme that includes a 65-kDa scaffolding A subunit (Aα or Aβ), a 36-kDa catalytic C subunit, and variable regulatory B subunits. The C subunit of PP2A undergoes reversible methylation on its C terminus, which regulates the binding of B regulatory subunits and PP2A phosphatase activity. Different B subunits confer different properties of PP2A in dephosphorylating downstream substrates, by which PP2A mediates distinct cellular functions. Substantial evidence indicates that PP2A functions as a tumor suppressor through its ability to mediate the dephosphorylation and inactivation of a number of tumorigenic proteins, including Akt, ERKs, and RalA. Mumby M., Cell, 130, p. 21-4 (2007). The fact that all of these tumorigenic PP2A substrates are downstream targets of Ras suggests that a major tumor suppressive activity of PP2A is to antagonize Ras signaling. Thus, from a therapeutic perspective, developing small-molecule activators of PP2A activity represents a potentially effective strategy to counter Ras signaling and thereby re-sensitize prostate cancer cells to androgen ablation.

SUMMARY OF THE INVENTION

One aspect of the invention provides compounds according to formula I:

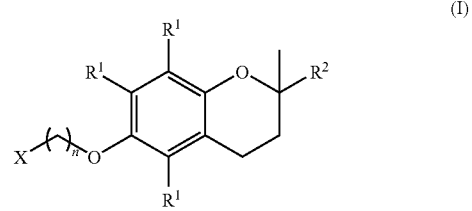

wherein $R^1$ is independently selected from hydrogen and methyl; $R^2$ is selected from the group consisting of 4,8-dimethyl-non-1-enyl, 4,8-dimethyl-nonyl, non-1-enyl, and nonanyl groups; X is a carboxyl, phosphonic, or sulfonic moiety, and n is an integer from 1 to 6, or a pharmaceutically acceptable salt thereof. These compounds affect dysregulated pathways such as the RAS signaling system in androgen receptor-dependent cancers such as hormone-refractory prostate cancer.

Another aspect of the invention provides pharmaceutical compositions including a compound of formula I or a pharmaceutically acceptable salt thereof, as an active ingredient, and a pharmaceutically acceptable liquid or solid carrier or carriers, in combination with the active ingredient. A further aspect of the invention provides a method of treating or preventing the development of androgen receptor-dependent cancer in a subject that includes administering a therapeutically effective amount of a composition including a compound of Formula I or a pharmaceutically acceptable salt thereof. Embodiments of this aspect of the invention may be used for treating prostate cancer, such as hormone-refractory prostate cancer. Yet another aspect of the invention provides a method of increasing protein phosphatase 2A (PP2A) activity by administering an effective amount of a compound of Formula I or a pharmaceutically acceptable salt thereof.

DETAILED DESCRIPTION OF THE INVENTION

Figure 1:
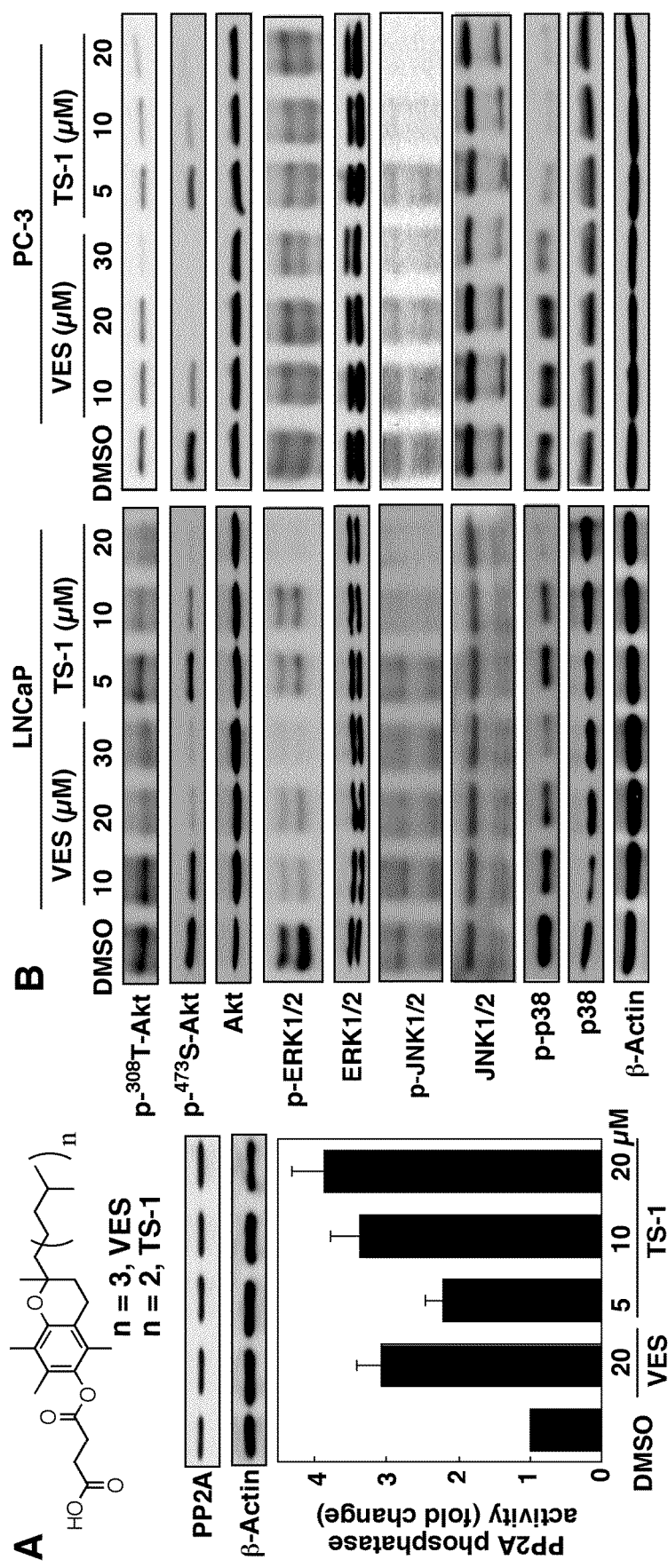
FIG. 1A, top, shows the structures of VES and TS-1, while the bottom provides a bar graph showing that VES and TS-1 increased PP2A phosphatase activity without affecting its expression.
FIG. 1B shows the effect of VES and TS-1 on facilitating the dephosphorylation of Akt and MAP kinases (ERKs, JNKs, and p38). Except for ERKs in PC-3, these kinases underwent marked dephosphorylation in drug-treated cells.

The inventors have demonstrated that VES and a number of tocopheryl derivatives mediate the dephosphorylation of Akt and MAP kinases in LNCaP and PC-3 cells through the activation of PP2A activity, as shown in FIG. 1. Accordingly, the inventors have developed a novel class of protein phosphatase 2A (PP2A)-activating agents based on α-tocopheryl succinate in view of the understanding that activation of PP2A phosphatase activity can delay or block cancer progression by antagonizing Ras-mediated oncogenic signaling pathways.

Since a major function of PP2A as a tumor suppressor is to antagonize Ras oncogenic signaling by downregulating the phosphorylation/activity of Ras targets, activation of PP2A activity by small-molecule agents represents a therapeutically relevant strategy to block cancer progression, and in particular prostate cancer progression.

DEFINITIONS

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for tocopheryl succinate derivatives are those that do not interfere with the tocopheryl succinate derivatives' anticancer activity. In the context of the present invention, the term "aliphatic group" means a saturated or unsaturated linear or branched hydrocarbon group. This term is used to encompass alkyl, alkenyl, and alkynyl groups, for example.

As used herein, a carboxyl moiety (COON) includes a hydroxyl moiety attached to a carbonyl group. A sulfonic moiety ($SO_3H$) is the defining portion of a sulfonic acid, and a phosphonic moiety ($PO_3H_2$) is the defining portion of a phosphonic acid.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups. Cyclic groups can be monocyclic or polycyclic and preferably have from 3 to 10 ring carbon atoms.

The term "truncated side chain," as used herein, refers to a phytyl side chain of a tocopheryl succinate derivative that has been shortened by the removal of one or more isopranyl units. Such truncated side chains are alkyl groups including from 1 to 11 carbon atoms. Examples of truncated side chains include 4,8-dimethyl-non-1-enyl, 4,8-dimethyl-nonyl, non-1-enyl, and nonanyl groups.

Unless otherwise specified, "alkylene" and "alkenylene" are the divalent forms of the "alkyl" and "alkenyl" groups defined above. The twins, "alkylenyl" and "alkenylenyl" are used when "alkylene" and "alkenylene", respectively, are substituted. For example, an arylalkylenyl group comprises an alkylene moiety to which an aryl group is attached.

The term "haloallyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoallyls, etc. On the other hand, the phrase "alkyl moiety" is limited to the inclusion of only pure open chain saturated hydrocarbon alkyl substituents, such as methyl, ethyl, propyl, tent-butyl, and the like.

The invention is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc.

Androgen receptor-dependent cancers are cancers that are dependent on the presence of androgen receptors on the cancer cells to maintain the ability of the cells to proliferate. For example, hormone refractory prostate cancer is an androgen receptor-dependent cancer in which an increased number of androgen receptors are provided in order to make the cells supersensitive to androgen and thereby able to proliferate even in an environment in which androgen levels have been decreased. See Chen et al. Nat. Med. 10, 33-39 (2004), which provides further description of the role of androgen receptors in cancer.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein refers to the partial or complete elimination of a potential effect, while inhibitors are compounds that have the ability to inhibit.

Tocopheryl Succinate Derivatives

The compounds of the present invention include a variety of different tocopheryl succinate derivatives. Tocopheryl succinate derivatives, as used herein, refer to compounds that are compounds described herein that are structurally related to tocopheryl succinate. However, the compounds do not have to be synthetically derived from tocopheryl succinate, and do not require a succinate side chain. Tocopheryl succinate derivatives of the invention include compounds according to formula (I):

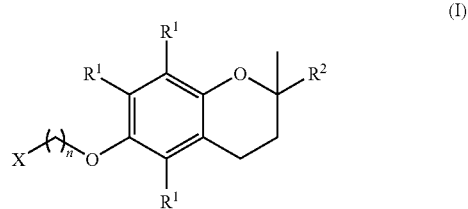

wherein $R^1$ is independently selected from hydrogen and methyl; $R^2$ is selected from the group consisting of 4,8-dimethyl-non-1-enyl, 4,8-dimethyl-nonyl, non-1-enyl, and nonanyl groups; X is a carboxyl, phosphonic, or sulfonic moiety, and n is an integer from 1 to 6.

The tocoperhyl succinate derivatives of the present invention have been shown and named herein without reference to stereochemistry. However, it is understood that vitamin E is [(2R)-2,5,7,8-Tetramethyl-2-[(4R,8R)-4,8,12-trimethyl-tridecyl]chroman-6-yl]acetate; i.e., a 2R isomer of the compounds shown, and that the 2R isomers may be preferred in embodiments of the invention. Accordingly, the tocopheryl succinate derivatives of the invention also include compounds according to formula (II):

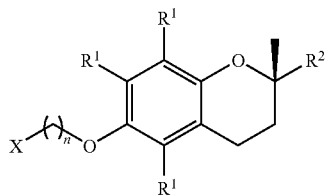

(II)

Wherein the various substituents are defined in the same manner as for formula (I).

In one embodiment, the tocopheryl succinate derivatives of formula (I) are defined such that $R^1$ is hydrogen, $R^2$ is a 4,8-dimethyl-non-1-enyl group, X is carboxyl moiety, and n is an integer from 1 to 6. These compounds are represented by formula (Ia) and include compounds selected from the group consisting of [2-(4,8-dimethyl-non-1-enyl)-2-methyl-chroman-6-yloxy]-acitic acid, 3-[2-(4,8-dimethyl-non-1-enyl)-2-methyl-chroman-6-yloxy]-propionic acid, 4-[2-(4,8-dimethyl-non-1-enyl)-2-methyl-chroman-6-yloxy]-butyric acid, 5-[2-(4,8-dimethyl-non-1-enyl)-2-methyl-chroman-6-yloxy]-pentanoic acid, 6-[2-(4,8-dimethyl-non-1-enyl)-2-methyl-chroman-6-yloxy]-hexanoic acid, and 7-[2-(4,8-dimethyl-non-1-enyl)-2-methyl-chroman-6-yloxy]-haptanoic acid.

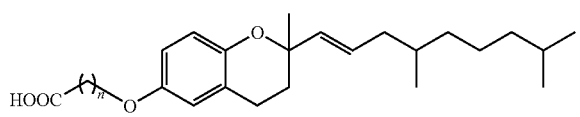

(Ia)

In another embodiment, the tocopheryl succinate derivatives of formula (I) are defined such that $R^1$ is hydrogen, $R^2$ is a 4,8-dimethyl-non-1-enyl group, X is a phosphonic moiety, and n is an integer from 1 to 6. These compounds are represented by formula (Ib) and include compounds selected from the group consisting of [2-(4,8-dimethyl-non-1-enyl)-2-methyl-chroman-6-yloxymethyl]-phosphonic acid, {2-[2-(4,8-dimethyl-non-1-enyl)-2-methyl-chroman-6-yloxy]-ethyl}-phosphonic acid, {3-[2-(4,8-dimethyl-non-1-enyl)-2-methyl-chroman-6-yloxy]-propyl}-phosphonic acid, {4-[2-(4,8-dimethyl-non-1-enyl)-2-methyl-chroman-6-yloxy]-butyl}-phosphonic acid, {5-[2-(4,8-dimethyl-non-1-enyl)-2-methyl-chroman-6-yloxy]-pentyl}-phosphonic acid, and {6-[2-(4,8-dimethyl-non-1-enyl)-2-methyl-chroman-6-yloxy]-hexyl}-phosphonic acid.

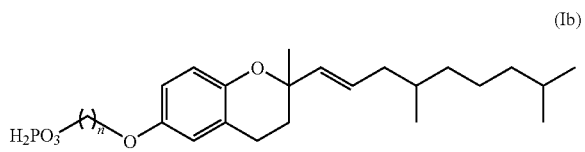 [SMILES: CC(C)CCCC(C)C/C=C/C1(C)CCc2cc(OCC(=O)O)ccc2O1]

(Ib)

In another embodiment, the tocopheryl succinate derivatives of formula (I) are defined such that $R^1$ is hydrogen, $R^2$ is a 4,8-dimethyl-non-1-enyl group, X is a sulfonic moiety, and n is an integer from 1 to 6. These compounds are represented by formula (Ic) and include compounds selected from the group consisting of [2-(4,8-dimethyl-non-1-enyl)-2-methyl-chroman-6-yloxy]-methanesulfonic acid; 2-[2-(4,8-dimethyl-non-1-enyl)-2-methyl-chroman-6-yloxy]-ethane-sulfonic acid; 3-[2-(4,8-dimethyl-non-1-enyl)-2-methyl-chroman-6-yloxy]-propane-1-sulfonic acid; 4-[2-(4,8-dimethyl-non-1-enyl)-2-methyl-chroman-6-yloxy]-butane-1-sulfonic acid; 5-[2-(4,8-dimethyl-non-1-enyl)-2-methyl-chroman-6-yloxy]-pentane-1-sulfonic acid; and 6-[2-(4,8-dimethyl-non-1-enyl)-2-methyl-chroman-6-yloxy]-hexane-1-sulfonic acid.

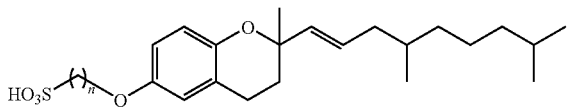

(Ic)

In another embodiment, the tocopheryl succinate derivatives of formula (I) are defined such that $R^1$ is hydrogen, $R^2$ is a 4,8-dimethyl-nonyl group, X is a carboxyl moiety, and n is an integer from 1 to 6. These compounds are represented by formula (Id) and include compounds selected from the group consisting of [2-(4,8-dimethyl-non-1-enyl)-2-methyl-chroman-6-yloxy]-acitic acid, 3-[2-(4,8-dimethyl-non-1-enyl)-2-methyl-chroman-6-yloxy]-propionic acid, 4-[2-(4,8-dimethyl-non-1-enyl)-2-methyl-chroman-6-yloxy]-butyric acid, 5-[2-(4,8-dimethyl-non-1-enyl)-2-methyl-chroman-6-yloxy]-pentanoic acid, 6-[2-(4,8-dimethyl-non-1-enyl)-2-methyl-chroman-6-yloxy]-hexanoic acid, 7-[2-(4,8-dimethyl-non-1-enyl)-2-methyl-chroman-6-yloxy]-haptanoic acid, and 8-[2-(4,8-dimethyl-non-1-enyl)-2-methyl-chroman-6-yloxy]-octanoic acid.

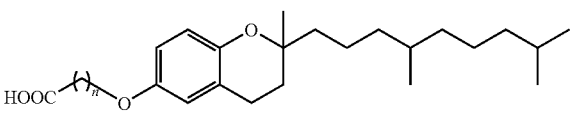

(Id)

In another embodiment, the tocopheryl succinate derivatives of formula (I) are defined such that $R^1$ is hydrogen, $R^2$ is a 4,8-dimethyl-nonyl group, X is a phosphonic moiety, and n is an integer from 1 to 6. These compounds are represented by formula (Ie) and include compounds selected from the group consisting of [2-(4,8-dimethyl-nonyl)-2-methyl-chroman-6-yloxymethyl]-phosphonic acid, {2-[2-(4,8-dimethyl-nonyl)-2-methyl-chroman-6-yloxy]ethyl}-phosphonic acid, {3-[2-(4,8-dimethyl-nonyl)-2-methyl-chroman-6-yloxy]-propyl}-phosphonic acid, {4-[2-(4,8-dimethyl-nonyl)-2-methyl-chroman-6-yloxy]-butyl}-phosphonic acid, {5-[2-(4,8-dimethyl-nonyl)-2-methyl-chroman-6-yloxy]-pentyl}-phosphonic acid, and {6-[2-(4,8-dimethyl-nonyl)-2-methyl-chroman-6-yloxy]-hexyl}-phosphonic acid.

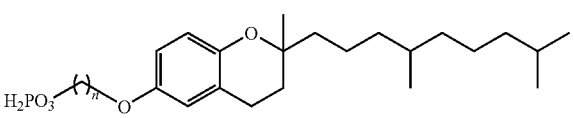

(Ie)

In another embodiment, the tocopheryl succinate derivatives of formula (I) are defined such that $R^1$ is hydrogen, $R^2$ is a 4,8-dimethyl-nonyl group, X is a sulfonic moiety, and n is an integer from 1 to 6. These compounds are represented by formula (If) and include compounds selected from the group consisting of [2-(4,8-dimethyl-nonyl)-2-methyl-chroman-6-yloxy]-methanesulfonic acid; 2-[2-(4,8-dimethyl-nonyl)-2-methyl-chroman-6-yloxy]-ethanesulfonic acid; 3-[2-(4,8-dimethyl-nonyl)-2-methyl-chroman-6-yloxy]-propane-1-sulfonic acid; 4-[2-(4,8-dimethyl-nonyl)-2-methyl-chroman-6-yloxy]-butane-1-sulfonic acid; 5-[2-(4,8-dimethyl-nonyl)-2-methyl-chroman-6-yloxy]-pentane-1-sulfonic acid; and 6-[2-(4,8-dimethyl-nonyl)-2-methyl-chroman-6-yloxy]-hexane-1-sulfonic acid.

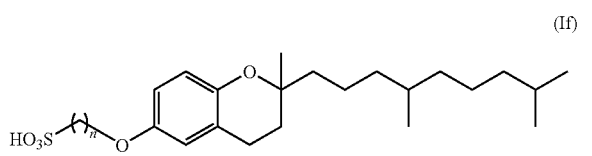 [SMILES: CC(C)CCCC(C)CCCC1(C)CCc2cc(OCS(=O)(=O)O)ccc2O1]

(If)

In another embodiment, the tocopheryl succinate derivatives of formula (I) are defined such that $R^1$ is hydrogen, $R^2$ is a non-1-enyl group, X is a carboxyl moiety, and n is an integer from 1 to 6. These compounds are represented by formula (Ig) and include compounds selected from the group consisting of (2-methyl-2-non-1-enyl-chroman-6-yloxy)-acetic acid; 3-(2-methyl-non-1-enyl-chroman-6-yloxy)-propionic acid, 4-(2-methyl-non-1-enyl-chroman-6-yloxy)-chroman-6-yloxy]-butyric acid, 5-(2-methyl-non-1-enyl-chroman-6-yloxy)-chroman-6-yloxy]-pentanoic acid, 6-(2-methyl-non-1-enyl-chroman-6-yloxy)-chroman-6-yloxy]-hexanoic acid, and 7-(2-methyl-non-1-enyl-chroman-6-yloxy)-chroman-6-yloxy]-heptanoic acid.

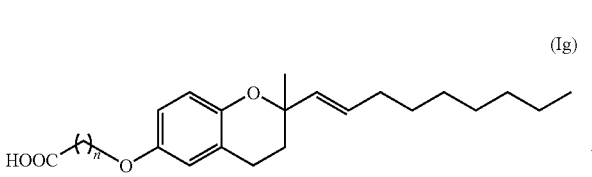

(Ig)

In another embodiment, the tocopheryl succinate derivatives of formula (I) are defined such that $R^1$ is hydrogen, $R^2$ is a non-1-enyl group, X is a phosphonic moiety, and n is an integer from 1 to 6. These compounds are represented by formula (Ih) and include compounds selected from the group consisting of (2-methyl-2-non-1-enyl-chroman-6-yloxymethyl)-phosphonic acid; [2-(2-methyl-2-non-1-enyl-chroman-6-yloxy)-ethyl]-phosphonic acid; [2-(2-methyl-2-non-1-enyl-chroman-6-yloxy)-propyl]-phosphonic acid; [2-(2-methyl-2-non-1-enyl-chroman-6-yloxy)-butyl]-phosphonic acid; [2-(2-methyl-2-non-1-enyl-chroman-6-yloxy)-pentyl]-phosphonic acid; and [2-(2-methyl-2-non-1-enyl-chroman-6-yloxy)-hexyl]phosphonic acid.

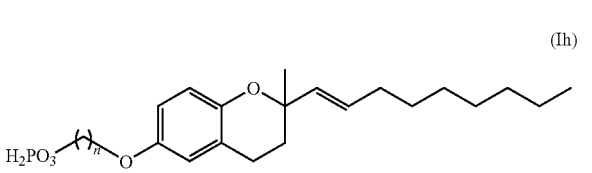

(Ih)

In another embodiment, the tocopheryl succinate derivatives of formula (I) are defined such that $R^1$ is hydrogen, $R^2$ is a non-1-enyl group, X is a sulfonic moiety, and n is an integer from 1 to 6. These compounds are represented by formula (Ii) and include compounds selected from the group consisting of 2-(2-methyl-2-non-1-enyl-chroman-6-yloxy)-methanesulfonic acid; 2-(2-methyl-2-non-1-enyl-chroman-6-yloxy)-ethanesulfonic acid; 2-(2-methyl-2-non-1-enyl-chroman-6-yloxy)-propane-1-sulfonic acid; 2-(2-methyl-2-non-1-enyl-chroman-6-yloxy)-butane-1-sulfonic acid; 2-(2-methyl-2-non-1-enyl-chroman-6-yloxy)-pentane-1-sulfonic acid; and 2-(2-methyl-2-non-1-enyl-chroman-6-yloxy)-hexane-1-sulfonic acid.

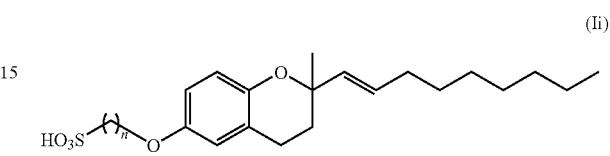

(Ii)

In another embodiment, the tocopheryl succinate derivatives of formula (I) are defined such that $R^1$ is hydrogen, $R^2$ is a nonanyl group, X is a carboxyl moiety, and n is an integer selected from 1 to 6. These compounds are represented by formula (Ij) and include compounds selected from the group consisting of (2-methyl-2-nonyl-chroman-6-yloxy)-acetic acid, 3-(2-methyl-nonyl-chroman-6-yloxy)-propionic acid, 4-(2-methyl-nonyl-chroman-6-yloxy)-chroman-6-yloxy]-butyric acid, 5-(2-methyl-nonyl-chroman-6-yloxy)-chroman-6-yloxy]-pentanoic acid, 6-(2-methyl-nonyl-chroman-6-yloxy)-chroman-6-yloxy]-hexanoic acid, 7-(2-methyl-nonyl-chroman-6-yloxy)-chroman-6-yloxy]-haptanoic acid, and 8-(2-methyl-nonyl-chroman-6-yloxy)-chroman-6-yloxy]-octanoic acid.

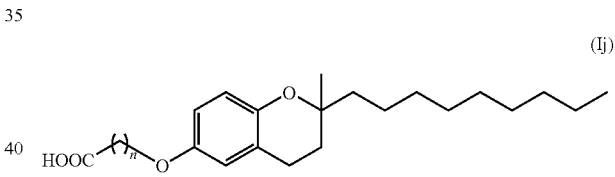

(Ij)

In another embodiment, the tocopheryl succinate derivatives of formula (I) are defined such that $R^1$ is hydrogen, $R^2$ is a nonanyl group, X is a phosphonic moiety, and n is an integer from 1 to 6. These compounds are represented by formula (Ik) and include compounds selected from the group consisting of (2-methyl-2-nonyl-chroman-6-yloxymethyl)-phosphonic acid; [2-(2-methyl-2-nonyl-chroman-6-yloxy)-ethyl]-phosphonic acid; [2-(2-methyl-2-nonyl-chroman-6-yloxy)-propyl]-phosphonic acid; [2-(2-methyl-2-nonyl-chroman-6-yloxy)-butyl]-phosphonic acid; [2-(2-methyl-2-nonyl-chroman-6-yloxy)-pentyl]phosphonic acid; and [2-(2-methyl-2-nonyl-chroman-6-yloxy)-hexyl]-phosphonic acid.

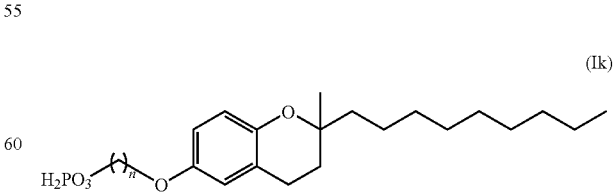

(Ik)

In another embodiment, the tocopheryl succinate derivatives of formula (I) are defined such that $R^1$ is hydrogen, $R^2$ is a nonanyl group, X is a sulfonic moiety, and n is an integer from 1 to 6. These compounds are represented by formula (Il)

and include compounds selected from the group consisting of (2-methyl-2-nonyl-chroman-6-yloxy)-methanesulfonic acid; (2-methyl-2-nonyl-chroman-6-yloxy)-ethanesulfonic acid; (2-methyl-2-nonyl-chroman-6-yloxy)-propane-1-sulfonic acid; (2-methyl-2-nonyl-chroman-6-yloxy)-butane-1-sulfonic acid; (2-methyl-2-nonyl-chroman-6-yloxy)-pentane-1-sulfonic acid; and (2-methyl-2-nonyl-chroman-6-yloxy)-hexane-1-sulfonic acid.

(II)
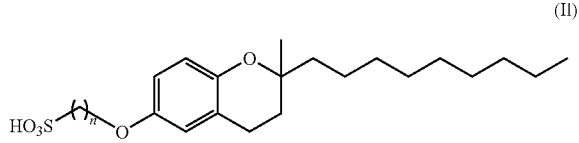 [SMILES: CCCCCCCCCC1(C)CCc2cc(OCS(=O)(=O)O)ccc2O1]

In another embodiment, the tocopheryl succinate derivatives of formula (I) are defined such that $R^1$ is methyl, $R^2$ is a 4,8-dimethyl-non-1-enyl group, X is a carboxyl moiety, and n is an integer from 1 to 6. These compounds are represented by formula (Im) and include compounds selected from the group consisting of [2-(4,8-dimethyl-non-1-enyl)-2,5,7,8-tetramethyl-chroman-6-yloxy]-acetic acid; 3-[2-(4,8-dimethyl-non-1-enyl)-2,5,7,8-tetramethyl-chroman-6-yloxy]-propionic acid; [2-(4,8-dimethyl-non-1-enyl)-2,5,7,8-tetramethyl-chroman-6-yloxy]-butyric acid; [2-(4,8-dimethyl-non-1-enyl)-2,5,7,8-tetramethyl-chroman-6-yloxy]-pentanoic acid; [2-(4,8-dimethyl-non-1-enyl)-2,5,7,8-tetramethyl-chroman-6-yloxy]-hexanoic acid; and [2-(4,8-dimethyl-non-1-enyl)-2,5,7,8-tetramethyl-chroman-6-yloxy]-heptanoic acid.

(Im)
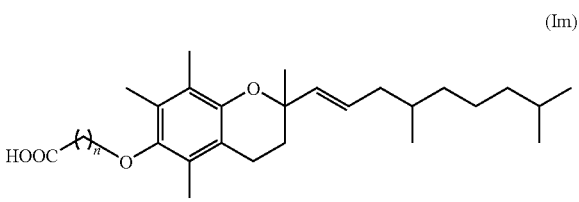 [SMILES: Cc1c(C)c2c(c(C)c1OCC(=O)O)CCC(C)(/C=C/CC(C)CCCC(C)C)O2]

In another embodiment, the tocopheryl succinate derivatives of formula (I) are defined such that $R^1$ is methyl, $R^2$ is a 4,8-dimethyl-non-1-enyl group, X is a phosphonic moiety, and n is an integer from 1 to 6. These compounds are represented by formula (In) and include compounds selected from the group consisting of [2-(4,8-dimethyl-non-1-enyl)-2,5,7,8-tetramethyl-chroman-6-yloxymethyl]-phosphonic acid; {2-[2-(4,8-dimethyl-non-1-enyl)-2,5,7,8-tetramethyl-chroman-6-yloxy]-ethyl}-phosphonic acid; {2-[2-(4,8-dimethyl-non-1-enyl)-2,5,7,8-tetramethyl-chroman-6-yloxy]-propyl}-phosphonic acid; {2-[2-(4,8-dimethyl-non-1-enyl)-2,5,7,8-tetramethyl-chroman-6-yloxy]-butyl}-phosphonic acid; {2-[2-(4,8-dimethyl-non-1-enyl)-2,5,7,8-tetramethyl-chroman-6-yloxy]-pentyl}-phosphonic acid; and {2-[2-(4,8-dimethyl-non-1-enyl)-2,5,7,8-tetramethyl-chroman-6-yloxy]-hexyl}-phosphonic acid.

(In)
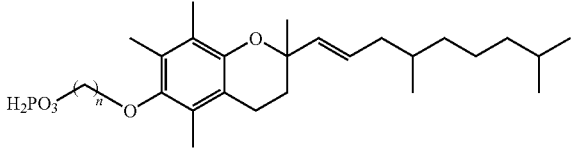

In another embodiment, the tocopheryl succinate derivatives of formula (I) are defined such that $R^1$ is methyl, $R^2$ is a 4,8-dimethyl-non-1-enyl group, X is a sulfonic moiety, and n is an integer from 1 to 6. These compounds are represented by formula (Io) and include compounds selected from the group consisting of 2-[2-(4,8-dimethyl-non-1-enyl)-2,5,7,8-tetramethyl-chroman-6-yloxy]-methanesulfonic acid; 2-[2-(4,8-dimethyl-non-1-enyl)-2,5,7,8-tetramethyl-chroman-6-yloxy]-ethanesulfonic acid; 2-[2-(4,8-dimethyl-non-1-enyl)-2,5,7,8-tetramethyl-chroman-6-yloxy]-propane-1-sulfonic acid; 2-[2-(4,8-dimethyl-non-1-enyl)-2,5,7,8-tetramethyl-chroman-6-yloxy]-butanesulfonic acid; 2-[2-(4,8-dimethyl-non-1-enyl)-2,5,7,8-tetramethyl-chroman-6-yloxy]-pentane-1-sulfonic acid; and 2-[2-(4,8-dimethyl-non-1-enyl)-2,5,7,8-tetramethyl-chroman-6-yloxy]-hexane-1-sulfonic acid.

(Io)
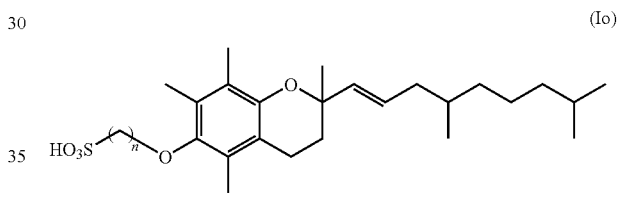

In another embodiment, the tocopheryl succinate derivatives of formula (I) are defined such that $R^1$ is methyl, $R^2$ is a 4,8-dimethyl-nonyl group, X is a carboxyl moiety, and n is an integer from 1 to 6. These compounds are represented by formula (Ip) and include compounds selected from the group consisting of [2-(4,8-dimethyl-nonyl)-2,5,7,8-tetramethyl-chroman-6-yloxy]-acetic acid; 3-[2-(4,8-dimethyl-nonyl)-2,5,7,8-tetramethyl-chroman-6-yloxy]-propionic acid; [2-(4,8-dimethyl-nonyl)-2,5,7,8-tetramethyl-chroman-6-yloxy]-butyric acid; [2-(4,8-dimethyl-nonyl)-2,5,7,8-tetramethyl-chroman-6-yloxy]-pentanoic acid; [2-(4,8-dimethyl-nonyl)-2,5,7,8-tetramethyl-chroman-6-yloxy]-hexanoic acid; and [2-(4,8-dimethyl-nonyl)-2,5,7,8-tetramethyl-chroman-6-yloxy]-heptanoic acid.

(Ip)
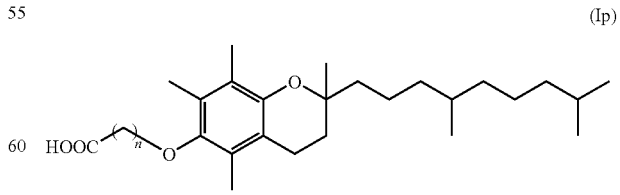

In another embodiment, the tocopheryl succinate derivatives of formula (I) are defined such that $R^1$ is methyl, $R^2$ is a 4,8-dimethyl-nonyl group, X is a phosphonic moiety, and n is an integer from 1 to 6. These compounds are represented by formula (Iq) and include compounds selected from the group consisting of [2-(4,8-dimethyl-nonyl)-2,5,7,8-tetramethyl-chroman-6-yloxymethyl]-phosphonic acid; {2-[2-(4,8-dimethyl-nonyl)-2,5,7,8-tetramethyl-chroman-6-yloxy]-ethyl}-phosphonic acid; {2-[2-(4,8-dimethyl-nonyl)-2,5,7,8-tetramethyl-chroman-6-yloxy]-propyl}-phosphonic acid; {2-[2-(4,8-dimethyl-nonyl)-2,5,7,8-tetramethyl-chroman-6-yloxy]-butyl}-phosphonic acid; {2-[2-(4,8-dimethyl-nonyl)-2,5,7,8-tetramethyl-chroman-6-yloxy]-pentyl}-phosphonic acid; and {2-[2-(4,8-dimethyl-nonyl)-2,5,7,8-tetramethyl-chroman-6-yloxy]-hexyl}-phosphonic acid.

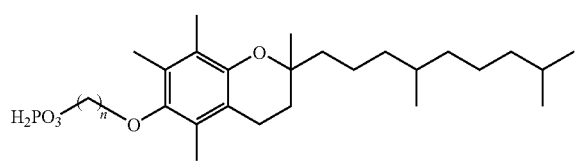

(Iq)

In another embodiment, the tocopheryl succinate derivatives of formula (I) are defined such that $R^1$ is methyl, $R^2$ is a 4,8-dimethyl-nonyl group, X is a sulfonic moiety, and n is an integer from 1 to 6. These compounds are represented by formula (Ir) and include compounds selected from the group consisting of 2-[2-(4,8-dimethyl-nonyl)-2,5,7,8-tetramethyl-chroman-6-yloxy]-methanesulfonic acid; 2-[2-(4,8-dimethyl-nonyl)-2,5,7,8-tetramethyl-chroman-6-yloxy]-ethanesulfonic acid; 2-[2-(4,8-dimethyl-nonyl)-2,5,7,8-tetramethyl-chroman-6-yloxy]-propane-1-sulfonic acid; 2-[2-(4,8-dimethyl-nonyl)-2,5,7,8-tetramethyl-chroman-6-yloxy]-butanesulfonic acid; 2-[2-(4,8-dimethyl-nonyl)-2,5,7,8-tetramethyl-chroman-6-yloxy]-pentane-1-sulfonic acid; and 2-[2-(4,8-dimethyl-nonyl)-2,5,7,8-tetramethyl-chroman-6-yloxy]-hexane-1-sulfonic acid.

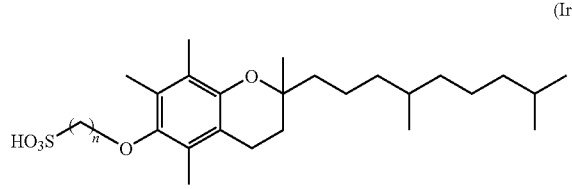

(Ir)

In another embodiment, the tocopheryl succinate derivatives of formula (I) are defined such that $R^1$ is methyl, $R^2$ is a non-1-enyl group, X is a carboxyl moiety, and n is an integer from 1 to 6. These compounds are represented by formula (Is) and include compounds selected from the group consisting of (2,5,7,8-tetramethyl-2-non-1-enyl-chroman-6-yloxy)-acetic acid; 3-(2,5,7,8-tetramethyl-2-non-1-enyl-chroman-6-yloxy)-propionic acid; 4-(2,5,7,8-tetramethyl-2-non-1-enyl-chroman-6-yloxy)-butyric acid; 6-(2,5,7,8-tetramethyl-2-non-1-enyl-chroman-6-yloxy)-pentanoic acid; and 7-(2,5,7,8-tetramethyl-2-non-1-enyl-chroman-6-yloxy)-heptanoic acid.

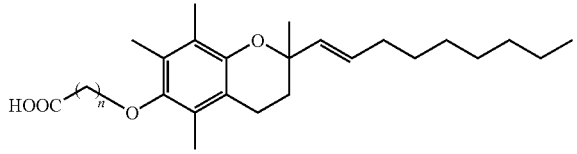

(Is)

In another embodiment, the tocopheryl succinate derivatives of formula (I) are defined such that $R^1$ is methyl, $R^2$ is a non-1-enyl group, X is a phosphonic moiety, and n is an integer from 1 to 6. These compounds are represented by formula (It) and include compounds selected from the group consisting of (2,5,7,8-tetramethyl-2-non-1-enyl-chroman-6-yloxymethyl)-phosphonic acid; [2-(2,5,7,8-tetramethyl-2-non-1-enyl-chroman-6-yloxy)-ethyl]-phosphonic acid; [2-(2,5,7,8-tetramethyl-2-non-1-enyl-chroman-6-yloxy)-propyl]-phosphonic acid; [2-(2,5,7,8-tetramethyl-2-non-1-enyl-chroman-6-yloxy)-butyl]-phosphonic acid; [2-(2,5,7,8-tetramethyl-2-non-1-enyl-chroman-6-yloxy)-pentyl]-phosphonic acid; and [2-(2,5,7,8-tetramethyl-2-non-1-enyl-chroman-6-yloxy)-hexyl]-phosphonic acid.

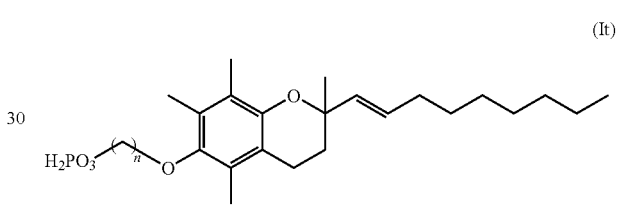

(It)

In another embodiment, the tocopheryl succinate derivatives of formula (I) are defined such that $R^1$ is methyl, $R^2$ is a non-1-enyl group, X is a sulfonic moiety, and n is an integer from 1 to 6, These compounds are represented by formula (Iu) and include compounds selected from the group consisting of (2,5,7,8-tetramethyl-2-non-1-enyl-chroman-6-yloxy)-methanesulfonic acid; 2-(2,5,7,8-tetramethyl-2-non-1-enyl-chroman-6-yloxy)-ethanesulfonic acid; 3-(2,5,7,8-tetramethyl-2-non-1-enyl-chroman-6-yloxy)-propanesulfonic acid; 4-(2,5,7,8-tetramethyl-2-non-1-enyl-chroman-6-yloxy)-butanesulfonic acid; 5-(2,5,7,8-tetramethyl-2-non-1-enyl-chroman-6-yloxy)-pentanesulfonic acid; and 6-(2,5,7,8-tetramethyl-2-non-1-enyl-chroman-6-yloxy)-hexanesulfonic acid.

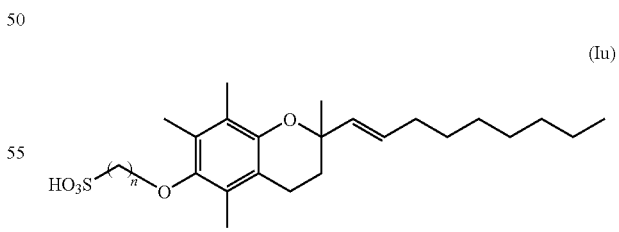

(Iu)

In another embodiment, the tocopheryl succinate derivatives of formula (I) are defined such that $R^1$ is methyl, $R^2$ is a nonyl group, X is a carboxyl moiety, and n is an integer from 1 to 6, These compounds are represented by formula (Iv) and include compounds selected from the group consisting of (2,5,7,8-tetramethyl-2-nonyl-chroman-6-yloxy)-acetic acid; 3-(2,5,7,8-tetramethyl-2-nonyl-chroman-6-yloxy)-propionic acid; 4-(2,5,7,8-tetramethyl-2-nonyl-chroman-6-yloxy)-butyric acid; 6-(2,5,7,8-tetramethyl-2-nonyl-chroman-6-yloxy)-pentanoic acid; and 7-(2,5,7,8-tetramethyl-2-nonyl-chroman-6-yloxy)-heptanoic acid.

(Iv)

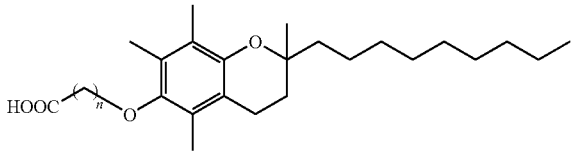

In another embodiment, the tocopheryl succinate derivatives of formula (I) are defined such that $R^1$ is methyl, $R^2$ is a nonyl group, X is a phosphonic moiety, and n is an integer from 1 to 6. These compounds are represented by formula (Iw) and include compounds selected from the group consisting of (2,5,7,8-tetramethyl-2-nonyl-chroman-6-yloxymethyl)-phosphonic acid; [2-(2,5,7,8-tetramethyl-2-nonyl-chroman-6-yloxy)-ethyl]-phosphonic acid; [2-(2,5,7,8-tetramethyl-2-nonyl-chroman-6-yloxy)-propyl]-phosphonic acid; [2-(2,5,7,8-tetramethyl-2-nonyl-chroman-6-yloxy)-butyl]-phosphonic acid; [2-(2,5,7,8-tetramethyl-2-nonyl-chroman-6-yloxy)-pentyl]-phosphonic acid; and [2-(2,5,7,8-tetramethyl-2-nonyl-chroman-6-yloxy)-hexyl]-phosphonic acid.

(Iw)

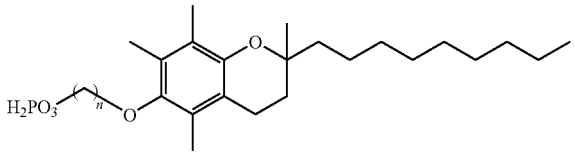

In another embodiment, the tocopheryl succinate derivatives of formula (I) are defined such that $R^1$ is methyl, $R^2$ is a nonyl group, X is a sulfonic moiety, and n is an integer selected from 1 to 6. These compounds are represented by formula (Ix) and include compounds selected from the group consisting of (2,5,7,8-tetramethyl-2-nonyl-chroman-6-yloxy)-methanesulfonic acid; 2-(2,5,7,8-tetramethyl-2-nonyl-chroman-6-yloxy)-ethanesulfonic acid; 3-(2,5,7,8-tetramethyl-2-nonyl-chroman-6-yloxy)-propanesulfonic acid; 4-(2,5,7,8-tetramethyl-2-nonyl-chroman-6-yloxy)-butanesulfonic acid; 5-(2,5,7,8-tetramethyl-2-nonyl-chroman-6-yloxy)-pentanesulfonic acid; and 6-(2,5,7,8-tetramethyl-2-nonyl-chroman-6-yloxy)-hexanesulfonic acid.

(Ix)

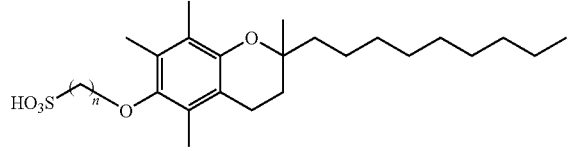

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers, including prostate cancer (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Treatment of Cancer Using Tocopheryl Succinate Derivatives

The present invention provides methods for treating or preventing the development of cancer in a subject using tocopheryl succinate derivatives. Cancer is a disease of abnormal and excessive cell proliferation. Cancer generally is initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as pre-cancerous cells. Cancer results in an increased number of cancer cells in a patient. These cells may form an abnormal mass of cells called a tumor, the cells of which are referred to as tumor cells. The overall amount of tumor cells in the body of a patient is referred to as the tumor load. Tumors can be either benign or malignant. A benign tumor contains cells that are proliferating but remain at a specific site. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Prostate cancer is cancer that initially develops in prostate tissue, but can metastasize to other tissues.

The tocopheryl succinate derivatives of the present invention can be used to treat various types of cancer and precancers. For example, the tocopheryl succinate derivatives can be used to androgen receptor-dependent cancers. The tocopheryl succinate derivatives can also be used to treat prostate cancer and hormone-refractory prostate cancer.

Treatment, as used herein, encompasses both prophylactic and therapeutic treatment. Tocopheryl succinate derivatives of the invention can, for example, be administered prophylactically to a subject in advance of the occurrence of cancer. Prophylactic administration is effective to decrease the likelihood of the subsequent occurrence of cancer in the subject, or decrease the severity of cancer that subsequently occurs. Alternatively, tocopheryl succinate derivatives of the invention can, for example, be administered therapeutically to a subject that is already afflicted by cancer (i.e., non-prophylactic treatment). In one embodiment of therapeutic administration, administration of the tocopheryl succinate derivatives is effective to eliminate the cancer; in another embodiment, administration of the tocopheryl succinate derivatives is effective to decrease the severity of the cancer or lengthen the lifespan of the subject so afflicted. The subject is preferably a mammal, such as a domesticated farm animal (e.g., cow, horse, pig) or pet (e.g., dog, cat). More preferably, the subject is a human.

The present invention also provides a method of increasing protein phosphatase 2A (PP2A) activity, that includes administering an effective amount of a composition including a compound of Formula I:

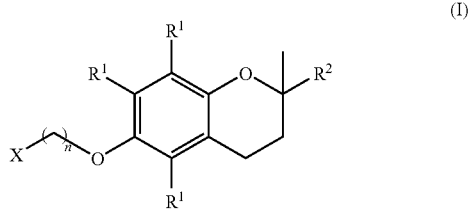

wherein $R^1$ is independently selected from hydrogen and methyl; $R^2$ is selected from the group consisting of 4,8-dimethyl-non-1-enyl, 4,8-dimethyl-nonyl, non-1-enyl, and nonanyl groups; X is a carboxyl, phosphonic, or sulfonic moiety, and n is an integer from 1 to 6, or a pharmaceutically acceptable salt thereof. Protein phosphatase 2A activity can be increased in a cell, which can be either in vivo or in vitro. Protein phosphate 2A activity can also be increased in a subject, including a subject with cancer. The ability to evaluate the effect of the compounds to activate PP2A can be evaluated using methods such as the PP2A immunoprecipitation phosphatase assay kit, as further described herein.

Figure 2:
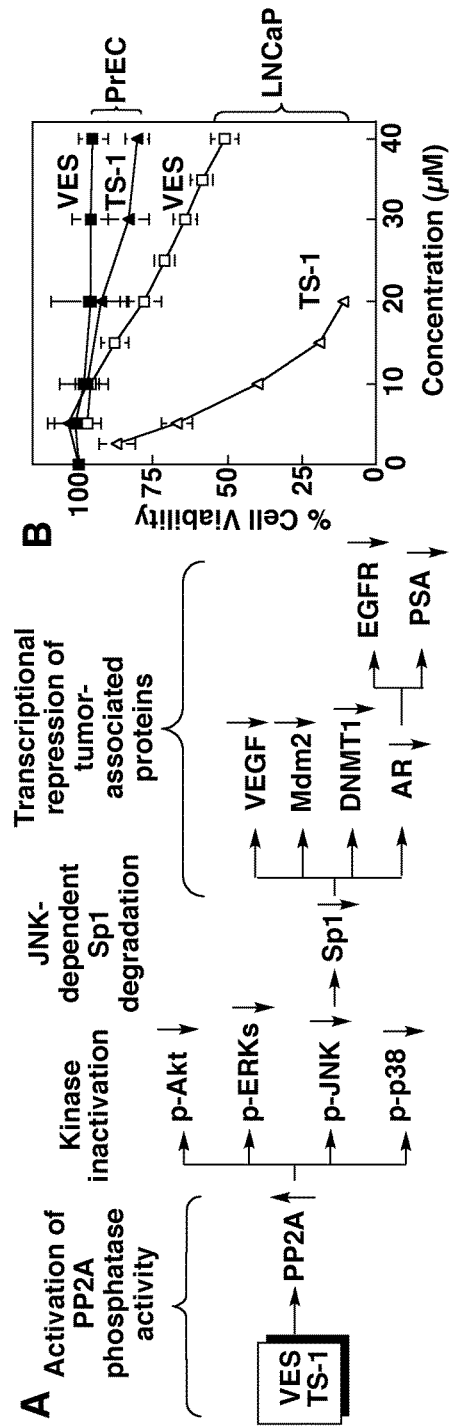
FIG. 2A provides a schematic model of the factors involved in the antitumor activities of VES and TS-1 through PP2A activation.
FIG. 2B provides a graph showing the effect of VES and TS-1 on suppressing the cell viability of LNCaP cells versus PrECs.

As shown in FIG. 2A, Inactivation of JNK by tocopheryl succinate derivatives facilitates the proteasomal degradation of Sp1, leading to the transcriptional repression of a series of signaling proteins pertaining to prostate carcinogenesis and tumor progression, including VEGF, Mdm2, DNMT1, and AR. From a mechanistic perspective, the ability of tocopheryl succinate derivatives to activate PP2A underscores their broad spectrum of pharmacological activities against many molecular targets. Equally important, relative to malignant cells, normal prostate epithelial cells (PrECs) were resistant to the antiproliferative effects of VES and TS-1, as shown in FIG. 2B.

Administration and Formulation of Tocopheryl Succinate Derivatives

The present invention also provides pharmaceutical compositions that include tocopheryl succinate derivatives according to formula I as an active ingredient, and a pharmaceutically acceptable liquid or solid carrier or carriers, in combination with the active ingredient. Any of the tocopheryl succinate derivatives described above as being suitable for the treatment of cancer can be included in pharmaceutical compositions of the invention.

The tocopheryl succinate derivatives can be administered without modification, or can be administered as pharmaceutically acceptable salts. Pharmaceutically acceptable salt refers to the relatively non-toxic, inorganic and organic acid addition salts of the tocopheryl succinate derivatives. These salts can be prepared in situ during the final isolation and purification of the tocopheryl succinate derivative, or by separately reacting a purified tocopheryl succinate derivative with a suitable organic or inorganic counterion, and isolating the salt thus formed. Representative cationic counterions suitable for use with tocopheryl succinate derivative anions include ammonium, arginine, diethylamine, ethylenediamine, piperazine, and the like. (See, for example, Handbook of Pharmaceutical Salts: Properties, Selection, and Use, P. H. Stahl and C. G. Wermuth (Eds), Wiley (2008)).

The pharmaceutical compositions include one or more tocopheryl succinate derivatives together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The tocopheryl succinate derivatives can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the tocopheryl succinate derivatives, or as a solution or suspension in an aqueous liquor or non-aqueous liquid such as a syrup, an elixir, an emulsion, or a draught. Such compositions and preparations typically contain at least about 0.1 wt-% of the active agent. The amount of tocopheryl succinate derivative (i.e., the active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Tocopheryl succinate derivatives of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Combinatorial synthesis was used to prepare a focused compound library based on the initial TS-1 structure. Structurally, TS-1 can be divided into three sub-structures, i.e., structure A, the acid moiety; structure B, the heterocyclic ring system; and structure C, the aliphatic side chain. These three components can be individually modified and then conjugated to generate new tocopheryl succinate derivatives. The respective substructures prepared are summarized in FIG. 3.

Figures 3, 4:
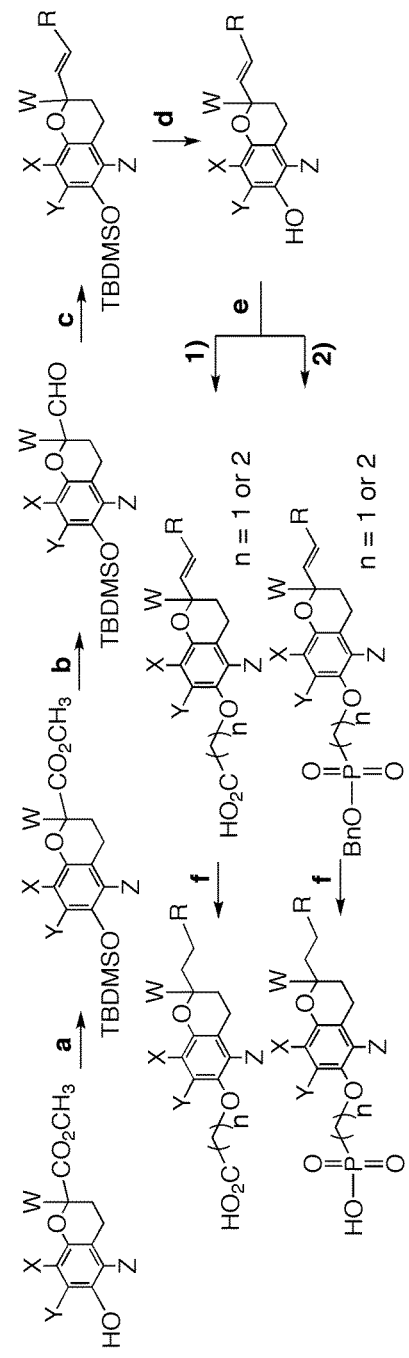
FIG. 3 provides a table showing the three components with varying structures involved in the combinatorial synthesis of tocopheryl succinate derivatives via coupling.
FIG. 4 provides a synthetic scheme for tocopheryl succinate derivatives.

The substructures serve differing functions in the tocopheryl succinate derivatives. For substructure A, the hemisuccinate (an ester linkage) is replaced by an ether-linked acid, i.e., a carboxylic acid ($—CO_2H$), a phosphonic acid ($—P(O)_2OH$), or a sulfonic acid ($—SO_3H$) to provide improved oral bioavailability. The ether linked acids can be attached at the end of an alkyl group with a variety of lengths, such as lengths of 1-6 methylene groups. While the ether linkage improves the bioavailability of the tocopheryl succinate derivatives, it has been shown to have little effect on the activity of the compounds themselves, outside of their improved bioavailability. For substructure B, structural variants of the chroman ring of TS-1 with different stereochemical properties can be used. For example, the chroman ring can be "clean" (i.e., not have any attached groups other than hydrogen atoms) or it can have one or more attached methyl groups. For substructure C, the chain length can be varied, the methyl branches removed, and an $\alpha,\beta$-double bond can be introduced to increase the rigidity of the side chain. Synthesis of these derivatives can be accomplished as illustrated in FIG. 4, which is amenable to scale-up to multi-grams quantities in a laboratory setting.

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

Vitamin E Succinate Derivative Mediate the Transcriptional Repression of the Androgen Receptor in Prostate Cancer Cells by Targeting the PP2A-JNK-Sp1 Signaling Axis Materials and Methods
Reagents, Antibodies, and Plasmids.

VES and the proteasome inhibitors MG132 and epoxomicin were purchased from EMD Chemicals, Inc (San Diego, Calif.) and Aldrich-Sigma (St. Louis, Mo.), respectively. TS1 {succinic acid mono-[2-(4,8-dimethyl-nonyl)-2,5,7,8-tetramethylchroman-6-yl]ester} is a truncated derivative of VES with an improved anti-proliferative potency. Shiau et al., J Biol Chem, 281, 11819-25 (2006). Stock solutions of these agents were made in DMSO and added to medium with a final DMSO concentration of 0.1%. Antibodies against various proteins were obtained from the following sources. Mouse monoclonal antibodies: AR and prostate specific antigen (PSA), Santa Cruz Biotechnology (Santa Cruz, Calif.). Rabbit antibodies: Sp1, Santa Cruz; poly(ADP-ribose)polymerase (PARP), p-Ser473-Akt, p-Thr308-Akt, Akt, p-ERK, ERK, p-JNK, JNK, p-p38, and p38, Cell Signaling Technology, Inc. (Beverly, Mass.). The AR promoter-luciferase reporter vector (hAR-Luc) was constructed as previously described. Yang et al., Cancer Res, 67, 3229-38 (2007). The dominant-negative JNK1 plasmid pCDNA3-Flag-JNK1a1 was obtained from Addgene Inc. (Cambridge, Mass.). Hemagglutinin (HA)-ubiquitin plasmid and the constitutively active INK plasmid Flag-MKK7-JNK1 encoding MKK7-JNK1 fusion protein with constitutive JNK activity (Lei et al., Mol Cell Biol., 22, 4929-42 (2002)) were kind gifts from Dr. Hung-Wen Chen (Institute of Biological Sciences, Academia Sinica, Taipei, Taiwan) and Dr. Roger Davis (University of Massachusetts Medical School, Worcester, Mass.), respectively. The pCMVSp1 plasmid was purchased from OriGene Technologies, Inc. (Rockville, Md.).

Cell Culture.

LNCaP androgen-dependent (p53$^{+/+}$) and PC-3 androgen-nonresponsive (p53$^{-/-}$) prostate cancer cells were purchased from the American Type Culture Collection (Manassas, Va.), and cultured in RPMI 1640 medium containing 10% heat-inactivated FBS. Normal prostate epithelial cells (PrECs) were obtained from Lonza, Inc. (Allendale, N.J.), and maintained in Prostate Epithelial Growth Media supplemented with a growth factor kit suggested by the vendor. All cell types were cultured at 37° C. in a humidified incubator containing 5% $CO_2$. Cells in log phase growth were harvested by trypsinization for use in the MTT viability assay. LNCaP cells were plated in poly-D-lysine coated culture flasks in order to assist cell adherence to the surface. Prior to drug treatment, cells were plated in a density of 12,000 cells/cm$^2$ surface area in the respective culture medium for 24-48 h, followed by individual test agents in 2.5% FBS-supplemented RPMI medium.

Immunoblotting.

Cells cultured in T25 flasks were collected by scraping, and cell pellets were washed once with PBS. Cells were lysed in a lysis buffer consisting of 1% SDS, 10 mM EDTA and 50 mM Tris-HCl, pH 8.1, in the presence of a commercial protease inhibitor cocktail from Aldrich-Sigma (2 mM AEBSF, 1 mM EDTA, 130 µM bestatin, 14 µM E-64, 1 µM leupeptin, and 0.3 µM aprotinin). Following a 10-sec sonication using 20% output in a Virsonic 300 sonicator (Virtis, Gardiner N.Y.) to disrupt cellular organelles and genomic DNA, cell lysates were centrifuged at 15,200×g for 15 minutes. One µL of the suspension was used for protein determination using a colorimetric BCA assay (Pierce, Rockford, Ill.), and to the remaining solution was added an equivalent volume of 2×SDS-polyacrylamide gel electrophoresis sample loading buffer (62.5 mM Tris-HCl, pH 6.8, 4% SDS, 5% β-mercaptoethanol, 20% glycerol, and 0.1% bromophenol blue), and boiled for 5 min. Equal amounts of proteins were resolved in 8% SDS-polyacrylamide gels, and transferred to nitrocellulose membranes using a semidry transfer cell. The transblotted membrane was washed twice with Tris-buffered saline containing 0.1% Tween 20 (TBST). After blocking with TBST containing 5% nonfat milk for 40 min, the membrane was incubated with the appropriate primary antibody in TBST-1% nonfat milk at 4° C. overnight. All primary antibodies were diluted 1:1000 in 1% nonfat milk-containing TBST. After treatment with the primary antibody, the membrane was washed three times with TBST for a total of 15 min, followed by incubation with goat anti-rabbit or anti-mouse Immunoglobulin G (IgG)-horseradish peroxidase conjugates (diluted 1:2000) for 1 h at room temperature and four washes with TBST for a total of 1 h. The immunoblots were visualized by enhanced chemiluminescence.

RNA Isolation and Reverse Transcription (RT)-PCR.

LNCaP cells were subject to total RNA isolation by using a Trizol reagent (Invitrogen Corporation, CA). RNA concentrations were determined by measuring absorption at 260 nm in a spectrophotometer. Aliquots of 2 µg of total RNA from each sample were reverse transcribed to cDNAs using the iScript cDNA Synthesis Kit (Bio-Rad) according to the manufacturer's instructions. PCR products were resolved electrophoretically in 1.2% agarose gels and visualized by ethidium bromide staining.

Transfection and Luciferase Assay.

Cells were transfected with 5 µg of the AR-linked luciferase reporter (hAR-Luc) plasmid in an Amaxa Nucleofector using a cell line-specific nucleofector kit according to the manufacturer's protocol (Amaxa Inc. Gaithersburg, Md.) and then seeded in T25 flasks at 3×10$^5$ cells per flask for 48 h.

The transfection efficiency was determined by transfecting cells with 3 µg of pmaxGFP plasmid followed by fluorescence microscopy to detect green fluorescent protein expression. For each transfection, herpes simplex virus (HSV) thymidine kinase promoter-driven *Renilla reniformis* luciferase was used as an internal control for normalization. For the luciferase reporter gene assay, after transfection, cells were cultured in 24-well plates in 10% FBS-supplemented RPMI 1640 for 48 h, subjected to different treatments in 2.5% FBS-supplemented medium for the indicated times, collected, and lysed with passive lysis buffer (Promega). Aliquots of lysates (50 µL) were mixed with 75 µL of luciferase substrate (Promega) in 96-well plates, and luciferase activities were monitored in a MicroLumaPlus LB96V luminometer (Berthold Technologies, Oak Ridge, Tenn.) with the WinGlow software package. All transfection experiments were carried out in six replicates.

Immunoprecipitation.

LNCaP cells were co-transfected with 5 µg each of Flag-Sp1 and HA-ubiquitin plasmids in an Amaxa Nucleofector using a LNCaP-specific nucleofector kit. These transiently transfected cells were seeded in 6-well plates at 2×10$^5$ per well. After 48-h incubation, cells were exposed to VES or TS-1 at the indicated concentration for 48 h, and lysed by a radioimmunoprecipitation assay lysis buffer (Santa Cruz Biotechnology) in the presence of a freshly prepared cocktail of phosphatase and protease inhibitors (2 mmol/L AEBSF, 1 mM EDTA, 130 µM bestatin, 14 µM E-64, 1 µM leupeptin, and 0.3 µM aprotinin, 2 mM imidazole, 1 mM sodium fluoride, 1.15 mM sodium molybdate, 1 mM sodium orthovanadate, and 4 mmol/L sodium tartrate dihydrate). After centrifugation at 13,000×g for 15 min, the supernatants were collected, preincubated with protein A/G agarose (Santa Cruz Biotechnology) for 15 min, and centrifuged at 1,000×g for 5 min. Supernatant (20 µL) were stored at 4° C. to be used as input, whereas the remaining supernatant was exposed to 4 µg of anti-Sp1 antibodies at 4° C. for 12 h, followed by protein A/G agarose beads at 4° C. for another 2 h. After brief centrifugation, immunoprecipitates were collected, washed with the aforementioned lysis buffer four times, suspended in 2×SDS sample buffer, and subjected to Western blot analysis with antibodies against HA and Flag.

Chromatin Immunoprecipitation (ChIP).

After drug treatment, LNCaP cells (2×10$^7$) in 50 mL of PBS were cross-linked with 1.35 mL of 37% formaldehyde (final concentration 1%) for 15 min at room temperature. Glycine solution (1 mol/L) was added to a final concentration of 125 mmol/L to stop the cross-linking reaction. Cells were harvested and washed twice with 5 mL of PBS, and the cell pellets were lysed in a ChIP lysis buffer containing (50 mM HEPES-KOH at pH 7.5, 140 mM NaCl, 1% Triton X-100, 0.1% sodium deoxycholate, 2 mM AEBSF, 1 mM EDTA, 130 µM bestatin, 14 µM-64, 1 µM leupeptin, and 0.3 µM aprotinin). The suspension was sonicated at 20% output in a Virsonic 300 sonicator with 6 sets of 10-sec pulses (resulting in an average fragment size of 0.8-0.2 kb) and centrifuged for 10 min at 15,000×g at 4° C. One-µL aliquots of the transparent supernatants were taken for determining protein concentrations by BCA assays. Immunoprecipitation was carried out as described above. Aliquots of 1 mg proteins were used for immunoprecipitation using 4 µg of anti-Sp1 antibody followed by protein A/G agarose beads. The immunoprecipitates were successively washed twice with 1 mL of ChIP lysis buffer, twice with 1 mL of a high salt CHIP lysis buffer (50 mmol/L HEPES-KOH at pH 7.5, 500 mmol/L NaCl, 1% Triton X-100, 0.1% sodium deoxycholate, 2 mmol/L AEBSF, 1 mmol/L EDTA 130 µmol/L bestatin, 14 µmol/L E-64, 1

μmol/L leupeptin, and 0.3 μmol/L aprotinin), twice with 1 ml of CHIP wash buffer (10 mmol/L Tris pH 8.0; 250 mmol/L LiCl; 0.5% NP-40; 0.5% sodium deoxycholate; 1 mmol/L EDTA), and twice with 1 mL of TE buffer (10 mmol/L Tris, pH 7.5, 1 mmol/L EDTA). The immunocomplex was eluted by addition of 75 μL of elution buffer (50 mmol/L Tris, pH 8.0, 1% SDS, 10 mmol/L EDTA), and were incubated at 65° C. for 10 min. The resulting supernatant was collected after brief centrifugation, and the pellets were eluted again with another 75 μl of elution buffer. The combined supernatant was incubated at 65° C. overnight. Ten-μg aliquots (1%) of the original total proteins were added to 150 μl of elution buffer, and were incubated at 65° C. overnight as the input control. Finally, samples were processed for DNA purification using a PCR purification kit (Qiagen, Valencia Calif.), and the recovered DNA was eluted with 50 μL of 10 mM Tris-HCl, pH 8.5. One-μl aliquots were used for PCR with primers spanning two adjacent Sp1 binding sites on the AR promoter, located at 429-442 of 5'-UTR of the AR gene. Wang et al., Carcinogenesis, 27, 2124-32 (2006). E2TAK taq polymerase (Takara Bio, Inc.) and the corresponding buffer system were used for amplification of PCR products.

PP2A Activity Assay.

PP2A activity in drug-treated cells was determined by using a PP2A Immunoprecipitation Phosphatase Assay Kit (Millipore) according to the manufacturer's instructions. LNCaP cells were exposed to DMSO, VES, or TS-1 at the indicated concentrations in 2.5% FBS supplemented medium for 12 h, and subjected to cell lysis in a phosphate-free lysis buffer containing 20 mmol/L imidazole-HCl, pH 7.0, 2 mM EDTA, 2 mM EGTA, 2 mM AEBSF, 1 mM EDTA, 130 μM bestatin, 14 μM E-64, 1 μM leupeptin, and 0.3 μM aprotinin. The suspension was sonicated (Virtis) at 20% output for 10 sec, followed by centrifugation at 2000×g for 5 min. One-μL aliquots of the supernatants were taken for protein determination by BCA assays, and the remaining supernatants were used for phosphatase activity assays. Aliquots of cell lysates containing 400 μg of proteins were combined with 4 μg of anti-PP2Ac antibody (Millipore), to which was added PP2A assay buffer (20 mmol/L Hepes pH 7.0, 100 mM NaCl) to a final volume of 500 μL followed by 40 μL of Protein A-agarose. Mixtures were incubated at 4° C. for 2 h, and briefly centrifuged. The immunocomplexes were washed and used for the phosphatase activity assay. The amounts of PP2A in the immunocomplexes were determined semi-quantitatively by Western blotting.

Results

Differential Effect of VES and TS1 on Suppressing AR Expression in LNCaP Cells Versus Normal Prostate Epithelial Cells (PrECs).

Figure 5:
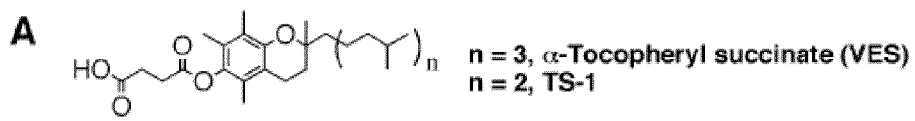
FIG. 5 shows the effect of VES and TS-1 on the transcriptional regulation of AR expression in LNCaP cells versus PrECs. Section (A) shows the structures of VES and TS-1. Section (B) shows the results of Western blot analysis of the dose- (upper) and time-dependent (lower) effects of VES and TS-1 on the expression of AR and its target gene products PSA and/or EGFR in LNCaP cells in 2.5% FBS-supplemented medium. Percentage values denote the relative intensity of protein bands of drug-treated samples to that of the respective DMSO vehicle-treated control after normalization to the respective internal reference β-actin. Each value represents the average of two independent experiments. Section (C), left, shows the RT-PCR analysis of the time-dependent suppressive effect of 10 µM VES or TS-1 on AR mRNA levels in LNCaP cells after 72-h incubation in 2.5% FBS-supplemented medium. Percentage values denote the relative intensity of mRNA bands of drug-treated samples to that of the respective DMSO vehicle-treated control after normalization to the respective internal reference β-actin. Each value represents the average of two independent experiments. The right side shows the dose-dependent inhibitory effect of VES and TS-1 on luciferase reporter activity in hAR-Luctransfected LNCaP cells after 72-h incubation in 2.5% FBS-supplemented medium. Columns, mean; bars, SD (n=6). Section (D), upper, shows the differential expression of AR in PrECs versus LNCaP cells, while the lower portion shows a Western blot analysis of the time-dependent effect of 10 µmol/L VES or TS-1 on the expression of AR and PSA in PrECs in 2.5% FBS-supplemented medium. Cells were exposed to 10 µmol/L VES or TS-1 for the indicated time intervals, and the expression levels of AR and PSA were analyzed by Western blot analysis. Section (E) shows the selective dose-dependent suppression of the viability of PrECs versus LNCaP cells by TS-1 after 72-h incubation in 2.5% FBS-supplemented prostate epithelial growth and RPMI 1640 media, respectively, as determined by MTT assays. Each data point represents mean+SD (n=6).
Figure 5:
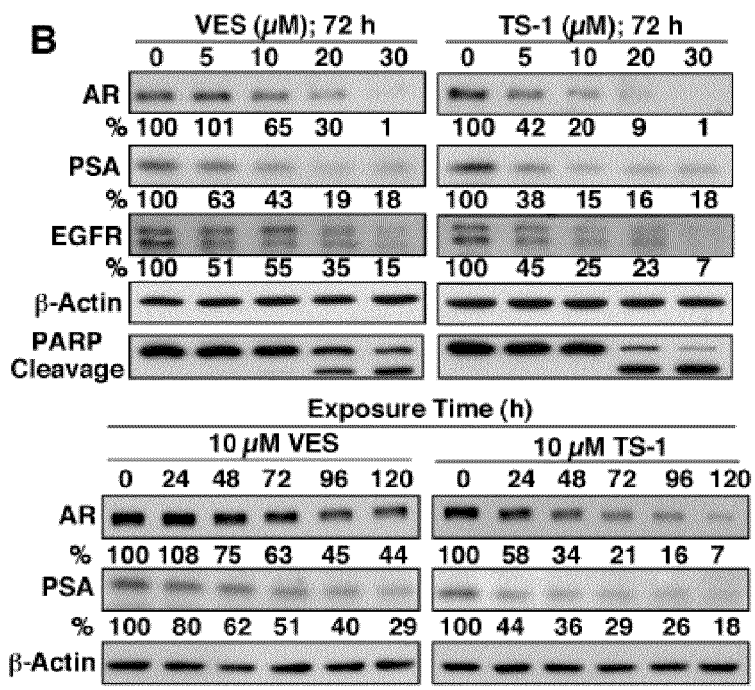
Figure 5:
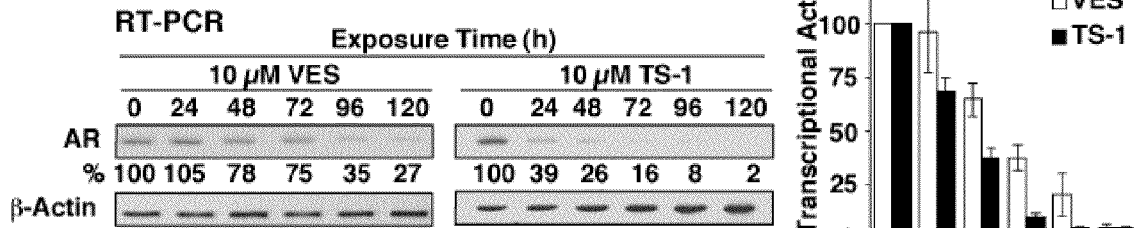
Figure 5:
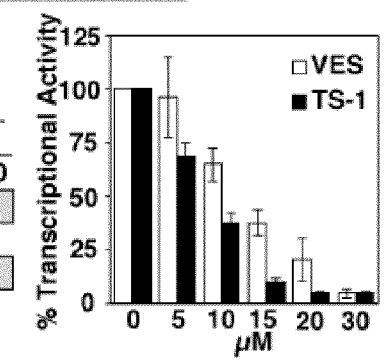
Figure 5:
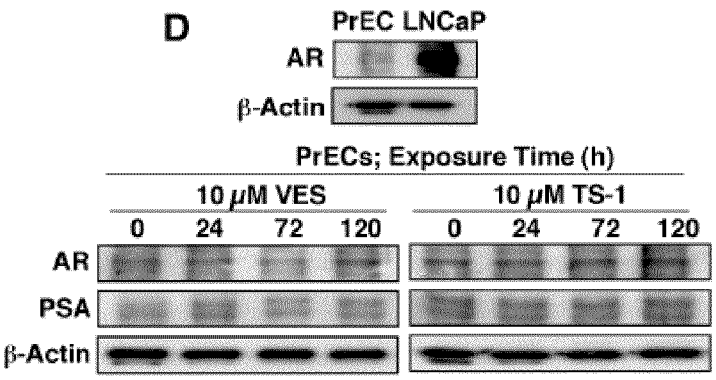

In the course of investigation of the inhibitory effect of VES on Bcl-xL/Bcl-2 function, a structurally optimized derivative, TS-1 (FIG. 5A), was developed in which the phytyl side chain was shortened by one isopranyl unit relative to that of VES. Shiau et al., J Biol Chem, 281, 11819-25 (2006) In this study, Western blot analysis indicates that this side chain truncation also led to higher potency in suppressing the expression of AR and its target gene product PSA in LNCaP cells (FIG. 5B). For example, TS-1 at 5 μmol/L was effectively reduced the expression of these biomarkers by 50% after 72 h of incubation, while VES required at least 10 μmol/L to achieve the same extent of suppression (FIG. 5B). The abilities of VES and TS-1 to repress AR correlated with the respective potencies in inducing apoptosis, as manifest by the extents of PARP cleavage. Furthermore, two lines of evidence reveal that this decrease in AR protein expression was attributed to the transcriptional inhibition of AR gene expression. First, RT-PCR analysis of the mRNA transcript of the AR gene in LNCaP cells showed a time-dependent reduction paralleling that of AR protein in response to 10 μM VES or TS-1 (FIG. 5C, left panel). Second, the AR promoter-luciferase reporter assay confirmed that these agents were able to inhibit AR gene transcription in a dose-dependent manner after 72 h of exposure (FIG. 5C, right panel). Together, these data indicate that VES and TS-1 mediated the inhibition of AR mRNA expression by targeting the transcriptional regulation of the AR promoter.

As compared to LNCaP cells, normal prostate epithelial cells (PrECs), which exhibited low abundance of AR, were resistant to the repressive effect of drug on AR expression (FIG. 5D). This selectivity might, in part, account for the differential sensitivity of normal versus malignant cells to the ability of TS-1 to suppress cell viability (FIG. 5E).

VES and TS-1 Target Sp1 to Downregulate AR Gene Transcription.

In a previous study of the effect of thiazolidinediones on modulating AR expression in LNCaP cells, the inventors demonstrated a mechanistic link between drug-mediated AR ablation and the downregulation of Sp-1 expression. Yang et al., Cancer Res, 67, 3229-38 (2007). To investigate this putative link in VES- and TS-1-induced AR repression, ChIP assays were performed to detect the binding of Sp1 to AR promoter in LNCaP cells treated with various doses of VES or TS-1 for 72 h. After formaldehyde treatment of cells, antibodies against Sp1 or IgG were used to immunoprecipitate Sp1-bound genomic DNA fragments, followed by PCR analysis with a pair of primers spanning the AR promoter. The results demonstrated that VES and TS-1 diminished the Sp1 binding to AR promoter in a dose-dependent manner. Based on Western blot analysis, this reduced binding was attributed to decreases in Sp1 expression in drug-treated cells. Moreover, this repression occurred at the posttranslational level since Sp1 mRNA expression remained unaltered even after treatment of LNCaP cells with high doses of VES and TS-1. The ability of VES and TS-1 to reduce Sp1 levels was confirmed by the dose-dependent transcriptional repression of a series of Sp1 downstream target genes, including those encoding vascular endothelial growth factor (VEGF), the negative p53 regulator Mdm2, and DNA methyltransferase 1 (DNMT1), all of which play important roles in prostate tumorigenesis and cancer progression.

Proteasomal Degradation of Sp1.

The ability of VES and TS-1 to modulate the stability of Sp1 protein was confirmed by its shortened half-life in drug-treated LNCaP cells relative to the DMSO control, which was more prominent after TS-1 treatment. Moreover, pharmacological inhibition of proteasomal degradation by epoxomicin and MG-132 protected Sp1 from TS-1-facilitated ablation. Because proteasome-facilitated proteolysis is preceded by ubiquitination, the formation of ubiquitinated Sp1 in response to different doses of VES and TS-1 in LNCaP cells expressing ectopic HA-ubiquitin and Flag-Sp1 was examined. After drug treatment for 24 h, cell lysates were immunoblotted with Sp1 antibodies or immunoprecipitated by anti-Flag antibody-agarose conjugates. Equivalent amounts of the immunoprecipitated proteins were subjected to immunoblotting with Flag or HA antibodies. Both TS-1 and VES increased the extent of Sp1 ubiquitination as indicated by a complex ladder of ubiquitinated Sp1 bands.

Ectopic Sp1 Expression Confers Resistance to the Effect of VES and TS-1 on AR Transcriptional Repression.

To validate the link between the drug-induced AR repression and Sp1 down-regulation, the ability of ectopic Sp1 expression to protect AR from VES- and TS-1-induced repression was assessed. Transient transfection of LNCaP cells with the pCMVSp1 plasmid resulted in a higher expression level of Sp1 than that of the pcDNA-transfected cells. Although treatment of pCMVSp1-transfected cells with 10 μM TS-1 or VES caused differential reduction in Sp1 expression, the respective Sp1 levels were still higher than that of untreated pcDNA-transfected cells. As a consequence, the expression level of AR remained virtually unchanged after drug treatment, indicating the protective effect of ectopic Sp1.

VES and TS-1 Mediate Sp1 Degradation Through a JNK-Dependent Pathway.

Despite recent advances in understanding Sp1's biological functions, the mechanism controlling the turnover of this transcription factor remains unclear. Data obtained by the inventors indicates that VES- and TS-1-facilitated Sp1 degradation was accompanied by concomitant reduction in its phosphorylation level. In light of a recent report that Jun $NH_2$-terminal kinases (JNKs) were involved in maintaining the stability of Sp1 (Chuang et al., Mol Biol Cell, 19, 1139-51 (2008)), this finding suggests a putative role of JNK in mediating the drug-induced Sp1 proteolysis. To corroborate this premise, the effect of VES and TS-1 on the phosphorylation status of JNKs and other kinases including Akt, ERK and p38 in LNCaP cells was examined. The results showed that treatment of LNCaP cells with VES and, to a greater extent, TS-1 led to a dose-dependent reduction in the phosphorylation levels of all four kinases examined, which was also noted in PC-3 cells. As these kinases are known PP2A substrates, their concomitant dephosphorylation raised a possible link with PP2A activation in drug-treated cells. This causal relationship was supported by the ability of VES and TS-1 to increase PP2A phosphatase activity. This enhancement in PP2A activity, however, was not due to increases in PP2A protein levels after drug treatment.

Furthermore, the mechanistic link between INK inactivation and Sp1 degradation was borne out by two lines of evidence. First, stable transfection of LNCaP cells with a dominant negative mutant of JNK1 (DN-JNK) mimicked the effect of VES and TS-1 on attenuating Sp1 expression. Second, PC-3 cells were used as a model to demonstrate that the constitutively active fusion protein MKK7-JNK1 conferred protection against VES- and TS-1-induced Sp1 degradation. Relative to PC-3 cells, LNCaP cells were vulnerable to the upregulation of this stress kinase as transient transfection of LNCaP cells with MKK7-JNK1 plasmids resulted in apoptotic death in nearly all transfected cells. Equally important, the PP2A inhibitor okadaic acid could protect cells from the suppressive effect of VES and TS-1 on the phosphorylation or expression of JNK, Sp1, and AR, confirming that VES and TS-1 facilitated the transcriptional repression of AR by targeting the PP2A-JNK-Sp1 signaling axis.

Discussion

In light of the therapeutic relevance of targeting AR in prostate cancer, the mechanism by which VES and its truncated derivative TS-1 suppress AR gene transcription was investigated. The data demonstrated that the effect of VES- and TS-1 on facilitating AR transcriptional repression was attributable to their ability to promote Sp1 degradation, which, in turn, was mediated through PP2A-mediated JNK inactivation. Equally important, relative to malignant cells, PrECs were resistant to the antiproliferative effects of VES and TS-1. From a mechanistic perspective, the function of VES and TS-1 to activate PP2A activity underscores their pleiotropic effects on targeting multiple signaling pathways. This study indicates that these mechanisms included, but were not limited to, those mediated by Akt, ERKs, JNKs, p38, Sp1, AR, and the respective downstream targets, all of which are clinically relevant to prostate carcinogenesis and tumor progression. Based on the ubiquitous action of PP2A in a growing list of phosphoproteins and signaling pathways, PP2A has been recognized as a tumor suppressor protein. Mumby, M., Cell, 130, 21-4 (2007). A recent study demonstrated that suppression of PP2A activity cooperates with other oncogenic changes to cause neoplastic transformation of multiple cell types. Junttila et al., 130, 51-62 (2007). Thus, the effect of VES and TS-1 to activate PP2A phosphatase activity is of translational value to develop novel PP2A-activating agents for prostate cancer therapy and prevention.

The PP2A-mediated downregulation of MAP kinases in VES/TS-1-treated prostate cancer cells, however, contrasts with recent reports that VES induced differentiation and apoptosis in breast and gastric cancer cells by activating ERKs and JNK. This discrepancy might be caused by differences in the regulation of the respective signaling networks in different cancer types. At present, the mechanism underlying the effect of VES and TS-1 on activating PP2A phosphatase activity remains unclear. It may be that. PP2A activation is attributable to increased intracellular levels of ceramide, a known PP2A activator, in drug-treated cells since VES has been reported to stimulate ceramide production. The ability of VES and TS-1 to mediate ceramide-induced PP2A activation is currently under investigation.

In summary, in the course of investigating the mechanism underlying VES- and TS-1-mediated suppression of AR gene transcription, the ability of these small molecule agents to modulate the PP2A-JNK-Sp1 signaling axis was demonstrated, of which the significance is multifold. First, this signaling axis provides a molecular basis to account for the broad spectrum of activities of VES on multiple signaling targets. This pleiotropic effect in conjunction with low toxicity is of clinical relevance to cancer therapy/prevention. Second, the higher potency of TS-1 relative to VES in modulating the PP2A-Sp1-AR signaling pathway demonstrates that these agents could be structurally optimized to develop potent PP2A-targeted agents for prostate cancer therapy.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to it the meaning of the text that follows the heading, unless so specified.

What is claimed is:

1. A compound according to formula I:

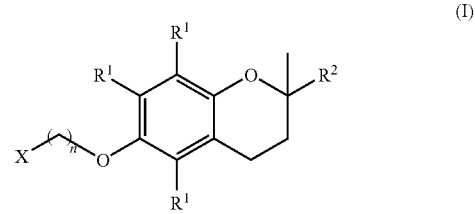

wherein $R^1$ is independently selected from hydrogen and methyl; $R^2$ is selected from the group consisting of 4,8- dimethyl-non-1-enyl, non-1-enyl, and nonanyl groups; X is a carboxyl, moiety, and n is an integer from 1 to 6, or a pharmaceutically acceptable salt thereof.

2. The compound of claim 1, wherein $R^2$ is a 4,8-dimethyl-non-1-enyl group.

3. The compound of claim 2, wherein X is a carboxyl moiety.

4. The compound of claim 1, wherein $R^2$ is a non-1-enyl group.

5. The compound of claim 4, wherein X is a carboxyl moiety.

6. The compound of claim 1, wherein $R^2$ is a nonanyl group.

7. The compound of claim 6, wherein X is a carboxyl moiety.

8. A method of treating the development of androgen receptor-dependent cancer in a subject, comprising administering a therapeutically effective amount of a composition including a compound of Formula I:

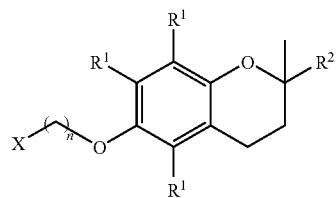

(I)

wherein $R^1$ is independently selected from hydrogen and methyl; $R^2$ is selected from the group consisting of 4,8-dimethyl-non-1-enyl, non-1-enyl, and nonanyl groups; X is a carboxyl, moiety, and n is an integer from 1 to 6, or a pharmaceutically acceptable salt thereof.

9. The method of claim 8, wherein the androgen receptor-dependent cancer is prostate cancer.

10. A method of increasing protein phosphatase 2A (PP2A) activity, comprising administering an effective amount of a composition including a compound of Formula I:

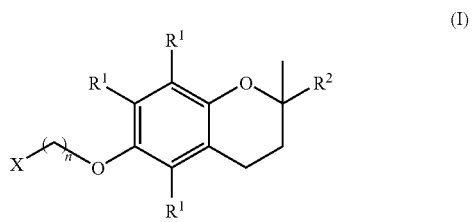

(I)

wherein $R^1$ is independently selected from hydrogen and methyl; $R^2$ is selected from the group consisting of 4,8-dimethyl-non-1-enyl, non-1-enyl, and nonanyl groups; X is a carboxyl moiety, and n is an integer from 1 to 6, or a pharmaceutically acceptable salt thereof.

* * * * *